(12) United States Patent
Liu

(10) Patent No.: US 9,962,403 B2
(45) Date of Patent: May 8, 2018

(54) FORMULATION DRUG OF SODIUM ION AND CALCIUM ION FOR TREATING CANCER, TUMOR AND NONMALIGNANCY

(71) Applicant: David Lexin Liu, South Boston, MA (US)

(72) Inventor: David Lexin Liu, South Boston, MA (US)

(73) Assignee: David Lexin Liu, South Boston, MA (US)

(*) Notice: Subject to any disclaimer, the term of this patent is extended or adjusted under 35 U.S.C. 154(b) by 19 days.

(21) Appl. No.: 14/361,818

(22) PCT Filed: Dec. 4, 2012

(86) PCT No.: PCT/US2012/067802
§ 371 (c)(1),
(2) Date: May 30, 2014

(87) PCT Pub. No.: WO2013/133873
PCT Pub. Date: Sep. 12, 2013

(65) Prior Publication Data
US 2014/0322359 A1   Oct. 30, 2014

Related U.S. Application Data

(60) Provisional application No. 61/566,655, filed on Dec. 4, 2011.

(51) Int. Cl.
*A61K 33/14* (2006.01)
*A61K 33/00* (2006.01)

(52) U.S. Cl.
CPC .............. *A61K 33/14* (2013.01); *A61K 33/00* (2013.01)

(58) Field of Classification Search
CPC ..... A61K 33/00; A61K 2300/00; A61K 33/14
See application file for complete search history.

(56) References Cited

U.S. PATENT DOCUMENTS

| 4,224,349 A * | 9/1980 | Gooch et al. ................. 426/281 |
| 2003/0087428 A1* | 5/2003 | Wolfinbarger et al. ....... 435/325 |
| 2010/0136140 A1* | 6/2010 | Zhao ............................ 424/680 |

OTHER PUBLICATIONS

Lin et al. (American Journal of Roentgenology, Jan. 2005, vol. 184, No. 1, 212-219).*

(Continued)

*Primary Examiner* — Aradhana Sasan

(57) ABSTRACT

The invention relates to a formulation cancer drug termed the "medicinal ion bomb" and its treatment methods. A mouse carcinoma, at 13mm x 13mm in size was killed by a single intratumoral injection with 0.14±ml of the "medicinal ion bomb". In selected human patient a solid cancer at 50mm x70mm in size was killed by one single intratumoral injection with 3.5±ml of the "medicinal ion bomb". The invention can be used as the first-line treatment of human cancer, in skin and subcutaneous tissue, brain, thyroid, breast, lung, liver, pancreas, prostate, and genital organs. The invention can also be used as the first-line treatment of human benign diseases of skin and subcutaneous neoplasm, breast fibrocystic change, benign prostatic hyperplasia and thyroid nodule.

6 Claims, 13 Drawing Sheets

3A

3B

3C

(56) References Cited

OTHER PUBLICATIONS

Ahmed et al. ("Improved Coagulation with Saline Solution Pretreatment during Radiofrequency Tumor Ablation in a Canine Model," Journal of Vascular and Interventional Radiology, vol. 13, Issue 7, Jul. 2002, pp. 717-724).*

Ehrlich H. (Geomicrobiology [e-book]. New York: CRC Press; 1996. Available from: eBook Collection (EBSCOhost), Ipswich, MA).*

Lin et al. ("Ablation of Liver Tumor by Injection of Hypertonic Saline," American Journal of Roentgenology, Jan. 2005, vol. 184, No. 1, 212-219).*

Nishikawa et al. ("Inhibitory effect of calcium chloride on gastric carcinogenesis in rats after treatment with N-methyl-N'-nitro-N-nitrosoguanidine and sodium chloride," Carcinogenesis vol. 13 No. 7 pp. 1155-1158, 1992).*

Oren ("Life at High Salt Concentrations," Prokaryotes (2006) 2:263-282).*

Rad et al. ("Effect of salinity on cell growth and β-carotene production in *Dunaliella* sp. Isolates from Urmia Lake in northwest of Iran," African Journal of Biotechnology vol. 10(12), pp. 2282-2289, Mar. 21, 2011).*

Siegle et al. ("Hypertonic Saline Destruction of Multiple Glomus Tumors," Journal of Dermatologic Surgery and Oncology 1994; 20: 347-348).*

Vogl et al., "Liver metastases: interventional therapeutic techniques and results, state of the art," European Radiology, 1999, 9, 675-684.*

Youk et al., "Therapeutic Response Evaluation of Malignant Hepatic Masses Treated by Interventional Procedures With Contrast-Enhanced Agent Detection Imaging," Journal of Ultrasound Medicine, 2003, 22: 911-920.*

Maddox, Thomas G, "Adverse Reactions to Contrast Material: Recognition, Prevention, and Treatment," American Family Physician, 2002, vol. 66, No. 7, pp. 1229-1234.*

* cited by examiner 1A  1B  1C 2A  2B  2C 3A  3B  3C 4A    4B    4C 5A    5B    5C 6A    6B    6C 7A  7B  7C 8A  8B  8C  8D 9A  9B  9C 10A   10B   10C 11A   11B   11C 12A   12B   12C 13A   13B   13C 14A    14B    14C 15A    15B    15C 16A    16B    16C 17A    17B    17C 18A    18B    18C 19A    19B    19C 20A  20B  20C  20D 21A  21B  21C 22A  22B  22C 23A      23B      23C 24A      24B 25A      25B      25C 25D  25E  25F 26A  26B  26C 28A  28B  28C 29A  29B  29C 30A  30B  30C  30D  30E 31A  31B  31C  31D 32A  32B  32C  32D 33A  33B  33C  33D 34A  34B  34C 35A  35B  35C 36A  36B  36C 37A  37B  37C 38A 38B 38C 39A 39B 39C 40A 40B 40C

FORMULATION DRUG OF SODIUM ION AND CALCIUM ION FOR TREATING CANCER, TUMOR AND NONMALIGNANCY

PRIORITY CLAIMS AND CROSS REFERENCE TO RELATED APPLICATION

This application is the U.S. national phase of and claim the benefit of priority from PCT/US12/67802, filed Dec. 4, 2012, which claims the benefit of priority from U.S. Provisional Application Ser. No. 61/566,655, filed Dec. 4, 2011, the entire content of each of which is incorporated herein by reference in its entirety.

TECHNICAL FIELDS OF THE INVENTION

The invention relates to a pharmaceutical cancer drug and its treatment method of intratumoral injection.

BACKGROUND OF THE INVENTION

Cancer is the uncontrolled growth of abnormal cells in the body. Cancer is often able to invade other tissues from its original location and spread to other parts of the body through blood and lymphatics. There are many types of cancer, which may be classified in pathology and clinical diagnosis into carcinoma, sarcoma, leukemia, lymphoma and myeloma, and malignant tumors of the central nervous system.

Cancer treatment remains a challenging endeavor to both the patient and healthcare provider. Current treatments include surgery, chemotherapy, radiotherapy, immunotherapy, biotherapy, laser therapy, cryotherapy, thermotherapy, etc. Significant advancements have been made in recent decades in cancer prevention and treatment cancer survival rates are still low for many types of cancers. It is estimated that in the U.S. alone, there are over 1.5 million new cases of cancer and more than half million of cancer-related deaths in 2011. Thus, cancer remains a major health threat to the public.

In two published reports, a single component of high concentration sodium chloride was used in treatment of tumors. In one report, Siegle et al. reportedly used hypertonic saline to treat one patient who had multiple glomus tumors, a rare benign neoplasm arising from the glomus body under fingernails and tympanic membrane. (Siegle, et al. *J. Dermatologic Surgery & Oncology* 20:347-348; 1994.) A single component of 23.4% sodium chloride solution was used, which did not result in successful treatment of the patient. This patient received 4 sessions of intralumenal injection with 23.4% hypertonic saline in 6 months. In another report, Lin et al. used 36.5% hypertonic saline to treat liver tumor in rabbits and none of the tumors were successfully treated. (Lin, et al. *Am. J. Roentgenology* 184: 212-219; 2005.)

Therefore, an urgent need remains for novel and effective treatments for cancer.

SUMMARY OF THE INVENTION

The invention is based, in part, on the discovery of a formulation cancer drug useful for treating various types of cancer, malignant tumor, benign tumor and nonmalignant disease and related methods of use.

The formulation cancer drug is termed the "medicinal ion bomb" that comprises five compositions of 5.0479 M of sodium ions ($Na^+$) (e.g., from sodium chloride (NaCl)), and 250 mM of calcium ions ($Ca^{2+}$) (e.g., from calcium chloride ($CaCl_2$)), 20 milligrams (mg) of adrenaline, 10 milliliters (ml) of Ultravist 370 and an appropriate amount of sterile distilled water that are in order mixed to make one liter (L) of the "medicinal ion bomb" solution (1 M=1 mol/L; 1 mM=$1 \times 10^{-3}$ M.).

The combination of $Na^+$ and $Ca^{2+}$ in the formulation of the "medicinal ion bomb" provides synergetic, complementary and dual-wave cancer-killing effects. Sterile distilled water is the dissolvent. The Ultravist 370 is an X-ray contrast medium for tracking the diffusion of the "medicinal ion bomb" solution inside a treated cancer or malignant tumor under computerized tomography (CT) scan guidance. Adrenaline is a vasoconstrictive drug that can make contraction of blood vessels to create a transient "artificial tumor capsule" in the treated tumor to prevent the "medicinal ion bomb" solution from flushing out of a non-capsulated tumor mass, reaching the enhancement of cancer killing treatment.

It has demonstrated that the "medicinal ion bomb" was capable of killing 18 types of human cancer cell lines in tissue culture within minutes. A human breast cancer in nude mouse, at 13 mm ×13 mm in size or equal to 3% of body weight, was killed by one single intratumoral injection with 0.14 ml of the "medicinal ion bomb." In selected human patients, a cancer lesion at 50 millimeters (mm)×70mm in size was killed by one single intratumoral injection with 3.5ml of the "medicinal ion bomb." The invention has been successfully applied in 78 human patients who suffered from 6 types of malignant tumor or cancer and 10 types of benign neoplasm or non-malignant conditions.

In one aspect, the invention generally relates to the effective treatment amount of $Na^+$ and $Ca^{2+}$ in treating a cancer, malignant tumor, benign tumor and nonmalignant disease via intratumoral injection. The composition include, in an aqueous solution, a $Na^+$ source providing a $Na^+$ concentration from about 2.0 M to about 5.5 M and a $Ca^{2+}$ source providing a $Ca^{2+}$ concentration from about 50 mM to about 6.0 M in the aqueous solution. The $Na^+$ source is NaCl and the $Ca^{2+}$ source is $CaCl_2$.

In another aspect, the invention generally relates to a formulation drug for treating a solid cancer or tumor is a saturated $Na^{30}$ and $Ca^{2+}$ aqueous solution, comprising about 5.0479 M of $Na^+$ and about 250 mM of $Ca^{2+}$ at room temperature.

In yet another aspect, the invention generally relates to a method for treating a cancer or tumor in a patient, comprising intratumoral injection or direct injection of the formulation cancer drug into a solid cancer or tumor lesion.

BRIEF DESCRIPTION OF THE DRAWINGS

FIG. 1A. A pretreatment tumor at 8mm×8mm in size. FIG. 1B. The standard procedure of intratumoral injection with the "medicinal ion bomb" in mouse. FIG. 1C. The mouse sarcoma was killed by a single injection with 0.10ml of the "medicinal ion bomb."

FIG. 2A. A pretreatment human breast cancer at 13mm×13mm in size that was equal to 3%± body weight of the mouse. FIG. 2B. The standard procedure of intratumoral injection with the "medicinal ion bomb" in mouse. FIG. 2C. The human breast cancer model in nude mouse was killed by a single intratumoral injection with 0.14ml of the "medicinal ion bomb."

FIG. 3A. Seven pretreatment cancer cells using the fluorescent labeled $Ca^{2+}$ probe. FIG. 3B. Two of 7 cancer cells were killed by the "medicinal ion bomb" in 14± seconds after starting treatment. FIG. 3C. All 7 cancer cells were killed in 18± seconds after starting treatment. The procedure of measuring the influx of $Na^+$ was the same as the abovementioned but use the fluorescent labeled $Na^+$ probe.

FIG. 4A. Pretreatment MCF7 human breast cancer cells as the self-control. FIG. 4B. Cancer cells treated were experiencing a vortex-like rotation in tissue culture in 5± seconds after adding the "medicinal ion bomb. " FIG. 4C. All cancer cells were killed in 16± seconds after starting treatment. Cancer cells in these 3 micrographs were from the same field. Magnification ×400.

" FIG. 5A. White lines surrounding cancer cells are sodium ions (salts) and calcium ions (salts) in the cancer tissue in mouse. Magnification ×1000. FIG. 5B. Cancer tissues treated were necrotic where the "medicinal ion bomb" reached. Magnification ×400. FIG. 5C. Multiple thrombi in a treated tumor section. Magnification ×400.

FIG. 6A. Control cancer cells. FIG. 6B. Membranes of cancer cells treated were broken into debris. FIG. 6C. Severely injured tumor vessels, particularly damages to the outer layer structure of arterioles and venules in tumor tissue. Multiple tumor vessels were transversely broken down.

FIG. 7A. Control cancer cells. FIG. 7B. Destroyed membrane, cytoskeleton, mitochondria, lysosome, nucleus and other organelles of a cancer cell treated with the "medicinal ion bomb. " FIG. 7C. Completely damaged outer layer, median layer and inner layer of a tumor vessel. An endothelial cell in the inner lumen of an arteriole was coming off. Magnifications ×2000.

FIG. 8A. A pretreatment tumor at 40mm×60mm in size in the patient's right shoulder. FIG. 8B. A pressure intratumoral injection with 3.0ml of the "medicinal ion bomb" to the tumor. FIG. 8C. The opening of the needle was upward. FIG. 8D. The opening of the needle was downward.

FIG. 9A. The pretreatment carcinoma was at 70mm×70mm in size. FIG. 9B. A single intratumoral injection with 26ml of the "medicinal ion bomb" was administered into the cancer lesion. FIG. 9C. This was a counterpart photo of the video image in 5 days after treatment. Macroscopically, the entire cancer lesion treated was completely dead. Microscopically, all cancer tissue was necrotic.

FIG. 10A. The pretreatment cancer was 15mm×15mm in size. The cancer was killed by one single intratumoral injection with 1.0ml of the "medicinal ion bomb. " FIG. 10B. The standard procedure of intratumoral injection with the "medicinal ion bomb" in human patient. FIG. 10C. Seven days after treatment, the cancer lesion developed coagulative necrosis that looked like a charred dead cancer remainder. The wound was healed without scar or defect by 2 weeks. A 3 year follow-up study showed no recurrence of the treated cancer.

FIG. 11A. The pretreatment tumor was 20mm× 20mm in size. FIG. 11B. The standard procedure of intratumoral injection with the "medicinal ion bomb" in human patient. FIG. 11C. Two tumors were killed by a single intratumoral injection with 0.5ml of the "medicinal ion bomb" in 3 days and the wound was healed by 2 weeks after treatment. A 3 year follow-up study showed no relapse of the tumor.

FIG. 12A. The pretreatment cancer was at 50mm×70mm in size. FIG. 12B. The cancer lesion was treated by one single intratumoral injection with 3.5ml of the "medicinal ion bomb. " FIG. 12C. The cancer was killed by 4 days and the wound was healed by 3 weeks.

FIG. 13A. A typical pretreatment butterfly-pattern melanoma in a human patient. FIG. 13B. A counterpart photo of the video image to demonstrate a single intratumoral injection with 1.2ml of the "medicinal ion bomb" into the melanoma. FIG. 13C. The melanoma was killed in days and the wound was healed by 3 weeks after treatment. A 9 year follow-up study showed no recurrence of the melanoma.

FIG. 14A. A pretreatment basal cell carcinoma at 12mm×12mm in size. FIG. 14B. The carcinoma regressed one week after a single intratumoral injection with 0.5ml of the "medicinal ion bomb. " FIG. 14C. The site of the carcinoma regressed carcinoma was healed by 3 weeks after treatment. An 8 year follow-up study showed no recurrence of the carcinoma.

FIG. 16A. An image of pretreatment mammography showed a large cyst at 40mm×40mm in size behind of the left nipple. Several small fibrocystic lesions were surrounding the large cyst. FIG. 16B. The mucosa fluid inside cyst was sucked, and the large cyst was repeatedly washed and sucked using the "medicinal ion bom" solution. Then, a single intra-cystic injection with 3.5ml of the "medicinal ion bomb" was given. FIG. 16C. The image of the posttreatment mammography to demonstrate that the breast fibrocystic disease was cured by 3 months after treatment.

FIG. 17A. The pretreatment tumor was 40mm×40mm in size. FIG. 17B. A single intratumoral injection with 2.0ml of the "medicinal ion bomb" was administered into the tumor. FIG. 17C. The tumor was cured by 8 weeks. A 9 year follow-up study showed no recurrence of the treated tumor.

FIG. 18A. A pretreatment atheroma in the vertex at 18mm×18mm in size. FIG. 18B. A counterpart photo of the video image showed a single intratumoral injection with 0.5ml of the "medicinal ion bomb. " FIG. 18C. The atheroma was cured. This photo was taken when a 9 year follow-up study was performed.

FIG. 20A. was a skin mole in a patient. FIG. 20B. A single intralesional injection with 0.2ml of the "medicinal ion bomb" was given. FIG. 20C. The mole developed coagulative necrosis by 7 days posttreatment. FIG. 20D. The skin mole was removed without scar or defect.

" FIG. 28A. The control membrane potential of a normal mouse cardiomyocyte in TyRode solution. FIG. 28B. A mouse cardiomyocyte died in 5± minutes after treatment with 5% concentration of the "medicinal ion bomb. " FIG. 28C. A mouse cardiomyocyte died in 3± minutes after treatment with 10% concentration of the "medicinal ion bomb." These data showed that killing action of the "medicinal ion bom " to cancer cells is a dose-and-time dependent.

FIG. 31A, pretreatment cancer cells as the control. FIG. 31B, cell morphology had slight changes in 3 seconds after starting treatment with the "medicinal ion bomb. " FIG. 31C. All cancer cells treated lost their normal morphology in 5-7 seconds after starting treatment. FIG. 31D. About 16 seconds after starting treatment with the "medicinal ion bomb", all cancer cells were killed or broken into cellular debris. Magnification ×200.

FIG. 32A. A pretreatment cancer cell as the self-control. FIG. 32B. Acute intracellular dehydration of the treated cancer cell by 6 seconds after starting treatment. FIG. 32C. The cancer cell was highly edema by 12 seconds after starting treatment. FIG. 32D. Ruptures of cell membrane and death of the cancer cell were seen by 16 seconds after starting treatment. Magnification ×400.

FIG. 33A. A pretreatment cancer cell as the control. FIG. 33B. Burst of a cancer cell resulted from highly edema treated by the "medicinal ion bomb. " FIG. 33C. Two treated cancer cells lost their cell outlines. FIG. 33D. Two cancer cells were damaged by the "medicinal ion bomb" that looked like rotten pineapples. Magnification ×400.

FIGS. 34A and 34B. Two tumor sections were fully filled with the "medicinal ion bomb. " FIG. 34C. Crystal compositions of $Na^+$ and $Ca^{2+}$ salts in intercellular gaps (white lines). Magnification ×1000.

" FIG. 35A. The pretreatment tumor as the control. FIG. 35B. A specimen taken from the margin of a treated tumor where there still was a small piece of area of living cancer tissue, indicating that the cancer tissue treated was not fully filled and killed by the "medicinal ion bomb", one of explanations of recurrent cancer. FIG. 35C. All tumor tissue in a mouse tumor model was completely killed, indicating that fully filling a cancer or tumor with the "medicinal ion bom " is a necessary factor to reach completely killing and preventing the cancer from recurrence. Magnification ×200.

FIG. 36A. All cancer tissues were completely killed. Red blood cells were lining on the inner lumen of tumor vessels, and inflammatory cells were seen. FIG. 36B. Multiple thrombi in tumor vessels in a tumor section. Magnification ×200. FIG. 36C. A typical thrombus in a small vein. Magnification ×400.

FIG. 37A. Untreated cancer cells as the control. Membranes of cancer cells were smooth. FIG. 37B. Innumerous cavernous pores in membranes of cancer cells treated. FIG. 37C. Cancer tissue treated with the "medicinal ion bomb" looked like volcanic crater characteristics. Magnification ×2000.

FIG. 38A. Control tumor vessels in an untreated tumor. The morphology of all tumor vessels was lotus-like and surface of these tumor vessels was smooth. Magnification ×1000. FIG. 38B. The outer layer, median layer and inner layer structures of tumor vessels underwent severe damages in a treated tumor. Multiple ruptures of arterioles and venules were seen. Magnification ×2000. FIG. 38C. A damaged large tumor vessel after treatment with the "medicinal ion bomb." A lot of protein materials and blood cell components deposited in an injured vascular lumen. Magnification ×1000.

FIG. 39A. Two untreated cancer cells as the control. FIG. 39B. A severely damaged cancer cell treated with the "medicinal ion bomb." Membrane, cytoplasm organelles, cytoskeleton, mitochondria, lysosome, nucleus and chromatins of the cell were fragmented. Magnification ×2000. FIG. 39C. This was a representative micrograph of TEM to demonstrate in viva distribution of the "medicinal ion bom " in a treated human breast cancer model in nude mouse. In this field there were 9 cancer cells. Four of them showed their entire cell morphology that looked like four pieces of Christmas hats. White brims surrounding 4 pieces of "Christmas hats" were the in vivo distribution of $Na^+$ and $Ca^{2+}$ salts in cancer tissue treated. Magnification ×2000.

FIG. 40A. The outer layer structures of vascular wall in an injured arteriole had multiple breaks and defects. Seven dark objects in the arteriole lumen were deformed red blood cells. Two red blood cells were crossing the defective vascular wall to the outside of the vascular lumen. Magnification ×2000. FIG. 40B. An injured endothelium was coming off from the inner wall of an arteriole. FIG. 40C. A damaged venule with multiple breaks. Magnification ×2000.

DETAILED DESCRIPTION OF THE INVENTION

Figure 1:
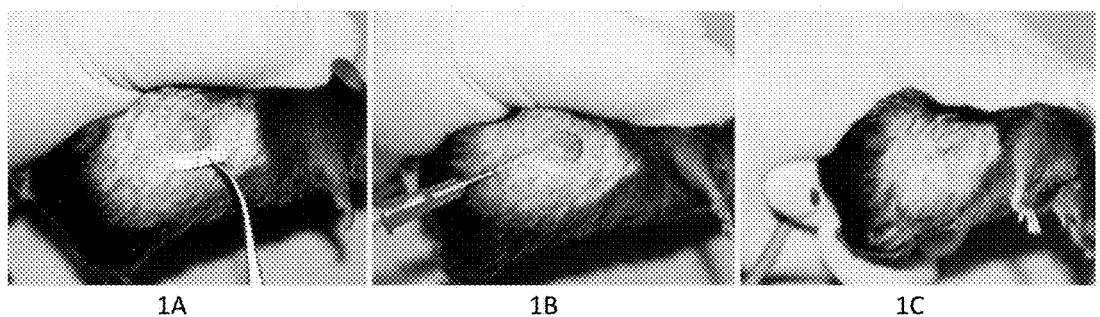
FIG. 1. A MCA207 mouse sarcoma model in C57BL6 mouse.

An occasional opportunity sparked this invention. Previously, the inventor used intratumoral injection of arsenic in experimental treatment of tumors in mice, which did not work well. One day, the inventor went shopping in a Chinese supermarket and bought a dozen salted duck eggs. On the way back home, he wondered why these salted duck eggs could be preserved at room temperature for years without rotting. The answer is that proteins and yolks in salted duck eggs are coagulated or clotted by high concentration of salt (sodium chloride), in particular by high concentration of sodium ions. The inventor linked this phenomenon to cell biology, cell physiology, membrane potential, ion science and cancer treatment, and presumed that high concentrations of sodium chloride might coagulate or clot proteins in cancer cells like what occurs in salted duck eggs.

A series of experiments were conducted using various solutions of high concentrations of sodium chloride, calcium chloride, and the "medicinal ion bomb" solution having both sodium and calcium ions. Three animal tumor models of MCA207 mouse sarcoma, MC38 mouse colorectal cancer and B16F1 mouse melanoma were established in C57BL6 mice. The treatment of intratumoral injection started when tumors reached 8mm×8mm in size.

Thirty-six C57BL6 tumor mice were randomly divided into three groups according to tumor types (12 animals in each group). Then, animals in each group were further divided into 4 subgroups (3 tumor mice in each subgroup). Tumor animals in subgroup-1, as the control, were treated by intratumoral injection with 0.1ml of normal saline. Tumor animals in subgroup-2 were treated by intratumoral injection with 0.1ml of various concentrations of sodium chloride solution. Tumor animals in subgroup-3 were treated by intratumoral injection with 0.1ml of various concentrations of calcium chloride solution. Tumor animals in subgroup-4 were treated with the "medicinal ion bomb" solution.

Twenty-four, 48 and 72 hours after treatment, experimental results were evaluated by measuring the dimension of necrotic area of the treated tumors using a ruler. No necrosis of tumors was seen in the control group. However, necrosis occurred in all tumors treated with high concentrations of sodium chloride solution, calcium chloride solution and the "medicinal ion bomb" solution. In representative examples, one single intratumoral injection with 0.1mL of 5.0479 M of sodium chloride solution caused average 90%± 5 necrosis of all treated tumors 48 hours posttreatment. One single intratumoral injection with 0.1ml of 250 mM, 1.0 M, 1.5 M, 2.0 M and 3.0 M of calcium chloride solutions caused coagulating necrosis of all treated tumors 48 hours posttreatment. One single intratumoral injection with 0.1 ml of the "medicinal ion bomb" solution reached 100% necrosis of all treated tumors 48 hours posttreatment.

Further, therapeutic effect of the "medicinal ion bomb" on 3 human cancer models was examined in nude mice, including U87 human glioblastoma, MCF7 human breast cancer and PC3 human prostate cancer. The number of nude mice, grouping of animals, and all experimental methods and injection doses in each subgroup were the same as in the C57BL6 mouse tumor models. The data showed that a single intratumoral injection with 0.1 ml of the "medicinal ion bomb" successfully removed the tumor in each of all 3 types of human cancer models in nude mice.

Intratumoral injection with the "medicinal ion bomb" was successfully applied in treating 78 human patients, including 6 types of malignant tumors or carcinoma (basal cell carcinoma, squamous cell carcinoma, maxillary carcinoma, melanoma, metastatic carcinoma from the penis and liver cancer) and 10 types of benign tumors (atheroma, lipoma, neoplasm, cyst, breast fibrocystic change, lymphadenopathy, thyroid nodule, genital tumor, skin mole, and cosmetics).

The "medicinal ion bomb" comprises two active components of $Na^+$ and $Ca^{2+}$ or two active compounds of sodium chloride and calcium chloride. The "medicinal ion bomb" comprises 5.0479 M of sodium chloride and 250 mM of calcium chloride and about 890ml of sterile distilled water. The route of administration of the "medicinal ion bomb" is via intratumoral injection (e.g., direct injection) of the "medicinal ion bomb" into tumor or cancer in the subject.

When sodium ion (e.g., NaCl) is used alone for intratumoral injection, the effective treatment concentration of $Na^+$ ranges from about 2.0 M to about 5.4414 M at room temperature. When calcium ion (e.g., $CaCl_2$) is used alone for intratumoral injection, the effective treatment concentration of $Ca^{2+}$ ranges from about 50 mM to 6.0 M at room temperature.

It is noted that the $Na^+$ source is not limited to NaCl, and the $Ca^{2+}$ source is not limited to $CaCl_2$. Other examples of $Na^+$ include inorganic or organic salts, for example, sodium bicarbonate, sodium carbonate, and sodium chlorate, et al.

Other sources of $Ca^{2+}$ include inorganic or organic salts, for example, calcium gluconate, calcium carbonate, and calcium acetate, et al.

There are a number of differences between the "medicinal ion bomb" compositions herein and two previous reports using a single component of sodium chloride. (1) This invention is to use ionic $Na^+$ and $Ca^{2+}$ in cancer treatment. However, previous reports used hypertonic saline. (2) The "medicinal ion bomb" includes up to five compositions in the specified amounts. The inventor discovered when $Na^+$ and $Ca^{2+}$ are combined in the pharmaceutical formulation of the "medicinal ion bomb" produces synergetic, complementary and dual-wave cancer-killing effects. (3) In this invention, calcium ions are used as the "enhancer" of cancer treatment because calcium ions are one of second messengers in cell signal transduction biology. Calcium ions also involve in the metabolism of many enzymes to activate protein kinase C and assist in the activation of another second messenger cAMP. Calcium ions regulate the protein calmodulin to produce an alpha helical structure. Therefore, slight increase in the amount of calcium ions in the intracellular fluid causes tremendous pathophysiological changes in the internal environment of cells and huge biological transformations in molecular regulation of cells, which cause either sickness or apoptosis or death of treated cancer cells. (4) The ion concentrations of the "medicinal ion bomb" disclosed herein are formulated on a large amount of experimental data. (5) In this invention, mechanisms of high concentration $Na^+$ and $Ca^{2+}$ to kill cancer cells have been verified from aspects of cell physiology, molecular biology, cellular membrane biology, membrane potential, ion channels, pathology, (SEM) and (TEM). (6) The invention herein has for the first time advanced treatment indications of intratumoral injection with the "medicinal ion bomb" and precision-guided intratumoral injection with the "medicinal ion bomb" for treating cancer, malignant tumor, benign tumor and nonmalignant disease in about nine human organs (skin and subcutaneous tissue, breast, prostate, thyroid, lung, liver, gential organs, brain and pancreas) and four categories of benign diseases (skin and subcutaneous neoplasm, breast fibrocystic changes, benign prostatic hyperplasia and thyroid nodules). (7) The route of administration of the "medicinal ion bomb" is via intratumoral injection or direct injection with the "medicinal ion bomb" into cancer lesion or tumor condition. (8) It is for the first time to use the concept and definition of the precision-guided intratumoral injection with the "medicinal ion bomb" in treatment of cancer and other benign diseases under CT scan or ultrasound guidance. (9) The concentration of $Na^+$ in the "medicinal ion bomb" solution is different from that of two previous reports (e.g., the formula of the claimed invention includes 5.0479 M of $Na^+$ (NaCl) and 250 mM of $Ca^{2+}$ ($CaCl_2$) in sterile distilled water to make the saturated ionic solution. (10) The invention of intratumoral injection with the "medicinal ion bomb" has been successfully used in treatment of 78 human patients who suffered from 6 types of cancer and 10 types of benign tumors and nonmalignant diseases. Therefore, clinical application of the invention in the treatment of types of diseases is different from that the previous reported.

As used herein, "benign tumor" refers to all of single or multiple solid tumors or neoplasm in pathologic classification including, but not limited to, adenoma, angioma, atheroma, fibroma, lipoma, teratoma, thyrophyma, cyst, polyp, skin mole, tag and wart, and other neoplasm conditions in human patients.

As used herein, "malignant tumor" refers to all of single or multiple solid malignancies in pathologic classification including, but not limited to, cancer, carcinoma, lymphoma, melanoma, myeloma, sarcoma, brain tumors and other malignant tumors in human patients.

Cell Physiology in Development of the "Medicinal Ion Bomb"

In cell physiology, survival of normal cells, tumor cells or cancer cells is dependent upon the equilibrium of osmotic pressure inside and outside of cells. Normal osmotic pressure of cells depends on the equilibrium of concentrations of ions between the extracellular and intracellular fluids. Physiologically, $Na^+$, $K^+$ and $Ca^{2+}$ play important roles in maintenance of living cells. When concentrations of ions between the extracellular and intracellular fluids are identical, it is called isotonic. Since the cell is at equilibrium, there is no ionic concentration gradient, and the flow of water in is equal to the flow of water out. This does not cause sickness or death of the cell. When a cell has a higher ionic concentration inside the cell than out, it is hypertonic. This causes a net flow of water into the cell. When a cell has a lower ionic concentration inside the cell than out, it is hypotonic and water flows out of the cell. (Costanzo LS, in Costanzo Physiology, $4^{th}$ edition, Saunders, Philadelphia, 2010.)

A significant change in concentrations of $Na^+$ and $Ca^{2+}$ between the extracellular and intracellular fluids causes tremendous transformations in physiology of cells that result in either sickness, apoptosis or death of cells. The "medicinal ion bomb" is intentionally designed to have high concentrations of $Na^+$ and $Ca^{2+}$ to kill cancer cell lines in tissue culture, cancer models in animals and large carcinomas in human patients.

One strategy is to deliver high concentrations of $Na^+$ and $Ca^{2+}$ to the extracellular fluid or intratumoral tissue where both ions can rapidly cross the membranes of cells to the intracellular fluid.

First, potential roles of $Na^+$, $K^+$, $Ca^{2+}$ and $Mg^{2+}$ in treatment of tumor and cancer were tested. In vivo experiments in BALB/c mice were performed. High concentration solutions of $Na^+$, $K^+$, $Ca^{2+}$ and $Mg^{2+}$ were injected intramuscularly. However, high concentrations of $K^+$ and $Mg^{2+}$ solutions are toxic and caused paralysis of legs, failure of cardiovascular and pulmonary systems, and death of animals. Experiments were focused on high concentrations of $Na^+$ and $Ca^{2+}$ solutions.

Different concentrations of sodium chloride solution were prepared, and the test started from 1.0 M, 1.5 M, 1.711 M, 3.0 M, 4.28 M, 4.449 M, 5.0479 M, 5.133 M to 5.4414 M. Various concentrations of calcium chloride solution were prepared, and the test started from 25 mM, 50 mM, 100 mM, 150 mM, 200 mM, 250 mM, 300 mM, 400 mM, 500 mM, 901 mM, and 1.0 M, 1.5 M, 2.0 M, 3.0 M, 4.0 M, 5.0 M, 5.5 M to 6.0 M.

After comparative studies, the formulation of the "medicinal ion bomb" was found to be 5.0479 M of $Na^+$ and 250 mM of $Ca^{2+}$ in about 890ml of sterile water, which is the saturated ionic solution of the combination of $Na^+$ and $Ca^{2+}$ at room temperature.

There are at least three rationales for choosing $Na^+$ to be the first active component of the "medicinal ion bomb." (1) $Na^+$ is an essential and safe ion and its concentration in the body is very flexible. Medicinal sodium chloride solutions have been long-term used for intravenous infusion in human patients. There is no evidence to show that $Na^+$ is toxic or a mutagenic agent when used in proper concentrations. (2) $Na^+$ has a unique feature of fast diffusion in living tissue and tumor tissue. As shown under the monitor of the real-time X-ray imaging in this invention, the diffusion of 5.0479 M of sodium chloride solution is approximately 25-fold faster than 1.0 M and 2.0 M of calcium chloride solution in human cancer model in nude mice. (3) As indicated, high concentrations of sodium chloride solutions are capable of killing multiple types of animal tumors in C57BL6 mice and human cancer models in nude mice.

In this study, $Ca^{2+}$ is used as the second active component of the "medicinal ion bomb." $Ca^{2+}$ is one of second messengers in cell signal transduction biology and its intracellular concentration is less than 0.0001 mM. The invention confirmed that the tissue culture medium containing 250 mM of $Ca^{2+}$ induced sickness, apoptosis and death of 18 types of human cancer cell lines. Fluorescence microscopy using the fluorescent labeled $Ca^{2+}$ probe technique demonstrated that 250 mM, 1.0 M, 1.5 M, 2.0 M and 3.0 M of $Ca^{2+}$ solutions caused immediate sickness or death of cancer cells.

Ex Vivo Killing Test of the "Medicinal Ion Bomb"

Roles of various concentrations of $Na^+$ and $Ca^{2+}$ solutions and the "medicinal ion bomb" solution were tested. Tumor cells were cultured in DMEM or RPMI1640 medium supplemented with 10% fetal bovine serum (FCS). The medium in the control group was free of the "medicinal ion bomb" solution. The "medicinal ion bomb" solution was added in all 18 experimental cancer groups. Mortality of cancer cells was evaluated by Trypan blue exclusion test or flow cytometry. The data showed that the "medicinal ion bomb" killed all 18 types of human cancer cell lines in tissue culture in 3 to 30 minutes, including A549 human lung cancer, ARO human thyroid cancer, CWR-22 human prostate cancer, HeLa human cervical cancer, HL60 human leukemia, HT-29 human colorectal cancer, Jurkat human T cell leukemia, K562 human leukemia, LNCap huma prostate cancer, M2 human lymphoma, M24 Human melanoma, MCF7 human breast cancer, MDA-MB-231 human breast adenocarcinoma, OVCAR3 human ovary cancer, PC3 human prostate cancer, SK-RC-52 human kidney cancer, T-47D human breast epithelial tumor, and U87 human glioblastoma.

Minimal and Maximal Effective Treatment Concentrations of $Na^+$ and $Ca^{2+}$

The in vivo treatment effect of the "medicinal ion bomb" was tested in 3 mouse tumor models. High concentrations of sodium chloride solution, calcium chloride solution, and the "medicinal ion bomb" solution were injected into MCA207 mouse sarcoma, MC38 mouse colorectal cancer and B16F1 mouse melanoma in C57BL6 mice. The data showed that when $Na^+$ solution was used alone or in combination for intratumoral injection its minimal effective treatment concentration is 2.0 M at room temperature. The 3.0 M concentration of $Na^+$ solution caused average 30%±10 necrosis of all treated tumors in 48 hours. One single intratumoral injection with 5.0479 M of $Na^+$ solution caused average 90%±5 necrosis of all treated tumors in 48 hours. The maximal effective treatment concentration of $Na^+$ (e.g., sodium chloride) solution was 5.4414 M at room temperature that caused average 92%±5 necrosis of all treated tumors in 48 hours. For intratumoral injection or direct injection into a tumor, the minimal effective treatment concentration of $Ca^{2+}$ (e.g., calcium chloride) solution was 50 mM at room temperature, and the maximal effective treatment concentration was 6.0 M at room temperature when it was used alone or in combination for intratumoral injection. However, high concentration of calcium chloride solution is toxic that causes unhealed wound at the injection site.

Diffusion of the "Medicinal Ion Bomb" in Tumor Tissue

Ex vivo diffusion experiments were performed in fresh beef liver at room temperature. Thirty parts of the "medicinal ion bomb" solution was mixed with one part of India ink. The mixed "medicinal ion bomb" solution was injected into beef livers starting from 1.0 ml, 2.0 ml and 3.0 ml. Sixty minutes after injection, beef livers were cut and dimensions of diffusion areas were measured with a ruler.

In vivo diffusion experiments were conducted in mice under the guidance of X-ray imaging. Ninety-nine milliliters of the "medicinal ion bomb" solution mixed with 1.0 ml of the X-ray contrast Ultravist 370, and 0.12 ml of the mixed "medicinal ion bomb" solution was injected into a human cancer model in nude mouse. Normally, a mouse tumor or human cancer model at 8mm×8mm to 10mm×10mm in size is fully filled with 0.12 ml of the mixed "medicinal ion bomb" solution in 3 to 5 minutes. The data demonstrated that the diffusion time and diffusion velocity of 5.0479 M of sodium chloride solution was approximately 25-fold faster than 1.0 M and 2.0 M of calcium chloride solution in tumor tissue in living mice.

Findings of the different diffusion time, different diffusion velocity and different diffusion dimension resulting from $Na^+$ and $Ca^{2+}$ solutions inspired the inventor to create the formula of the "medicinal ion bomb." The key idea of this invention was to develop a powerful "medicinal ion bomb" for treating cancer, malignant tumor, benign tumor and nonmalignant disease by the combination of $Na^+$ and $Ca^{2+}$. Because the diffusion of $Na^+$ is fast and the diffusion of $Ca^{2+}$ is slow in tumor tissue, and because both types of ions are capable of killing cancers when they are used separately, we found that the combination of $Na^+$ and $Ca^{2+}$ in the formulation of the "medicinal ion bomb" generated synergetic, complementary and dual-wave cancer-killing effects. The first wave of in vivo cancer-killing effect (the early killing action) was mediated by $Na^+$, which happened in one to 12 hours after treatment. The second wave of in vivo cancer-killing action (the later killing effect) was mediated by $Ca^{2+}$, which occurs in 6 to 24 hours after treatment.

Relationship between Influx of $Na^+$—$Ca^{2+}$ and Death of Cancer Cells

Three tracking techniques of ion channels were utilized to explain the relationship between influx of $Na^+$ and $Ca^{2+}$ from the extracellular fluid into intracellular fluid and death of cancer cells. The patch clamp technique is a commonly used method to measure the membrane potential of cardiomyocytes. Here, the patch clamp technique was used to demonstrate the relationship between changes in the membrane potential and death of mouse cardiomyocytes. Normal mouse cardiomyocytes were pre-cultured in the patch clamp chamber and membrane potentials were measured before and after adding the "medicinal ion bomb" solution. The membrane potential of mouse cardiomyocytes was automatically recorded. When 5% and 10% of the "medicinal ion bomb" media were added in the patch clamp chamber, mouse cardiomyocytes died in 5 and 3 minutes, respectively. When 100% of the "medicinal ion bomb" solution was added in the patch clamp chamber, mouse cardiomyocytes died in dozen seconds. The data indicated that cell-killing action of the "medicinal ion bomb" is a dose-and-time dependent.

Fluorescent labeled ion probe technique was used in study of the influx of $Na^+$ and $Ca^{2+}$ from the extracellular fluid into intracellular fluid of cancer cells. Before and after adding the "medicinal ion bomb" solution to the cell chamber, fluorescence image and time of the influx of $Na^+$ or $Ca^{2+}$ into cancer cells were real-time recorded. If a cancer cell is killed, the fluorescence image of the cancer cell labeled with Na$^+$ or Ca$^{2+}$ probe disappears from the computer screen, indicating that either the membrane of cancer cell is broken up or the entire cancer cell is busted. The fluorescent Na$^+$ probe image data showed that use of 5.0479 M of Na$^+$ solution alone took 20±4 seconds to kill MCF7 human breast cancer cells. When the "medicinal ion bomb" solution was used it took only 18±4 seconds to kill the same type of cancer cells, indicating that Ca$^{2+}$ have an enhancement effect in cancer treatment, and indicating that the formulation of the combination of Na$^+$ and Ca$^{2+}$ has synergetic and complementary cancer-killing effect.

The Nikon Diaphot inverted microscopy is a real-time imaging system for investigation of living cells. It is equipped with a video apparatus and a photograph unit. The video data revealed 5 pathologic phases of the "medicinal ion bomb" to kill cancer cells: (1) Rapid disruption of cancer cells; (2) acute dehydration of cancer cells because of high concentrations of Na$^+$ and Ca$^{2+}$ in the extracellular fluid after adding the "medicinal ion bomb;" (3) extremely swelling of cancer cells due to the overwhelming influx of large amount of Na$^+$ and Ca$^{2+}$ in the extracellular fluid from the "medicinal ion bomb" into intracellular fluid; (4) burst of cancer cells caused by extremely swollen cancer cells; and (5) immediate death of cancer cells. The entire process of 5 pathologic damages to cancer cells occurred in dozen seconds and each of pathologic phases occurred in only 3 to 4 seconds.

In physiological condition, concentrations of Na$^+$ in the extracellular fluid is 140 mM and intracellular fluid is 14 mM. Because the "medicinal ion bomb" solution has 5.0479 M of Na$^+$, the concentration of Na$^+$ in the extracellular fluid of cancer cells is 36-fold higher than its normal level and the concentration of Na$^+$ in the intracellular fluid is about 360-fold higher than its normal concentration. As a result, cancer cells are killed in dozen seconds by overwhelming influx of Na$^+$ from the "medicinal ion bomb" into cancer cells to break the equilibrium of concentration gradient of Na$^+$ between the extracellular fluid and intracellular fluid and the equilibrium of osmotic pressure inside and outside of cancer cells.

On the other hand, the normal concentration of Ca$^{2+}$ in the extracellular fluid is 2.5 mM and intracellular fluid is 0.0001 mM in mammalian cells. The "medicinal ion bomb" contains 250 mM of Ca$^{2+}$, which is 100-fold higher than its physiological level in the extracellular fluid and approximately 2.5 million-fold higher than its physiological concentration in the intracellular fluid. As a result, cancer cells are killed in dozen seconds by overwhelming influx of Ca$^{2+}$ from the "medicinal ion bomb" into cancer cells to break the equilibrium of concentration gradient of Ca$^{2+}$ between the extracellular fluid and intracellular fluid and the equilibrium of osmotic pressure inside and outside of cancer cells.

Pathological and Ultrastructural Studies

Twenty-four hours after treatment with the "medicinal ion bomb," specimens for microscopy, SEM and TEM were taken from nude mouse bearing MCF7 human breast cancer or patients whose cancer was treated with the "medicinal ion bomb." Tissues sections for pathologic examination were stained with hematoxylin and eosin and specimens for SEM and TEM were prepared according to the corresponding instructions.

Representative pathologic features of human cancer treated with the "medicinal ion bomb" include (1) sodium ions (salts) and calcium ions (salts) distributed in surrounding tissue of cancer cells; (2) necrosis of cancer tissues where the "medicinal ion bomb" reached, indicating that fully filling a cancer with the "medicinal ion bomb" solution is a necessary condition to reach completely killing; (3) multiple thrombi in tumor blood vessels; and (4) massive bleeding in necrotic areas resulting from injured tumor vasculatures.

SEM demonstrated that in vivo human breast cancer models treated with the "medicinal ion bomb" showed innumerous cavernous pores in cell membranes. Further, membranes of cancer cells were broken to pieces or debris. Outer layer tissues of tumor blood vessels came off. Multiple ruptures of arterioles or venules in tumor tissue were seen. TEM showed collapse of membranes, mitochondria, lysosome, and nucleus of cancer cells. Endothelial cells in the inner lining of tumor vessels were split off from the vascular lumen. Most of cancer cells were ruptured into several parts and interstitial tissue of the treated cancer was smashed. All these pathologic and ultrastructural features of treated mouse tumors and human cancer models in nude mice looked like the site of post-nuclear bombing.

Application of the "Medicinal Ion Bomb" in Human Patients

Amongst 78 human patients, 11 patients suffered from malignant tumors or cancer, including 2 cases of skin basal cell carcinoma, 3 cases of skin squamous cell carcinoma, 2 cases of melanoma, 1 case of maxillary adenocarcinoma, 1 case of metastatic cancer from the penis, and 2 cases of liver cancer. With the exception of one patient who suffered from terminal stage of maxillary carcinoma died in 3 months after treatment, other 10 cancer patients were successfully treated by one single intratumoral injection with the "medicinal ion bomb." Other 67 patients who suffered from 10 types of benign tumors and nonmalignant diseases (1 case of genital neoplasm, 1 case of thyroid nodule, 2 cases of lymphadenopathy, 3 cases of skin mole, 4 cases of cysts, 4 cases of breast fibrocystic changes, 6 cases of cosmetic conditions, 10 cases of neoplasm, 15 cases of atheroma and 21 cases of lipoma) were successfully treated.

When a cancer lesion is located in surface of the body or subcutaneous tissue, the cancer can be treated under direct view and no anesthesia is used. Patient is brought to a treatment table. After disinfection of the tumor area with 70% alcohol, a 19-gauge needle is placed into the center of cancerous tumor. The cancer lesion is treated by intratumoral injection with the "medicinal ion bomb". Special caution is taken not to punch through the opposite capsule of tumor. A proper injection pressure is maintained for 3 to 5 minutes to ensure the entire tumor is fully filled with the "medicinal ion bomb" solution. Generally, patient is uneventful throughout the course of treatment. Posttreatment studies were made in 7, 14, 21 and 28 days after treatment.

If a malignant tumor or cancer lesion is located in deep tissue or internal organ of the body, for example, brain tumor or pancreatic cancer, a general anesthesia is used. The precision-guided intratumoral injection with the "medicinal ion bomb" is performed under CT scan guidance to monitor if the entire tumor is fully filled with the "medicinal ion bomb" After treatment, patient is hospitalized for days and posttreatment studies are conducted in 7, 14, 21 and 28 days by CT scan to determine if the treated cancer lesion has reduced in size or completely killed.

Needles used for intratumoral injection are from 19 gauge to 26 gauge in size, and extra length indwelling catheter are used for a cancer or tumor in deep tissue or internal organ, depending on the size and location of tumor. Needles and extra-long indwelling catheters can be bent in any angle to reach a cancer or tumor lesion where a surgical access is unavailable or a cancer condition is inoperable.

A unique advantage of this invention is that intratumoral injection with the "medicinal ion bomb" can be used as the first-line treatment of cancer patients who may be cured or effectively treated without interventions for surgery, chemotherapy, and/or radiotherapy. On the other hand, the treatment provided herein may be combined with surgery, chemotherapy, radiotherapy, immunotherapy, biotherapy and other cancer treatments to enhance the therapeutic result of cancer treatment.

The formulation drug of $Na^+$ and $Ca^{2+}$ and treatment methods disclosed herein can be administered to cancer patient to kill a cancer lesion in situ before surgery. Then, a "dead cancer" is safely removed by surgery. Advantages of this strategy are to reduce risks of iatrogenic cancer metastases or intraoperative cancer tissue spreading from surgical procedure, which increase patient survival rate and tumor curability.

The formulation drug of $Na^+$ and $Ca^{2+}$ of the invention, when properly administered as disclosed herein, are not believed to cause side effect, such as inflammation, pyretogenesis, carcinogenesis, and mutagenesis.

The formulation drug of $Na^+$ and $Ca^{2+}$ and treatment methods of intratumoral injection with the "medicinal ion bomb" in the invention can be used as the first-line treatment in patients suffering from cutaneous and subcutaneous cancers and malignant tumors including, but not limited to, basal cell carcinoma, melanoma, sarcoma, skin cancer, and other skin malignant conditions. They can also be used as the first-line treatment in patients suffering from cutaneous and subcutaneous benign tumors including, but not limited to, adenoma, atheroma, hemangioma, lipoma, skin mole, tag and wart, and other neoplasm conditions.

The formulation drug of $Na^+$ and $Ca^{2+}$ and treatment methods of the invention can be used as the first-line treatment in patients suffering from brain tumors including, but not limited to, glioma, adenoma and other brain tumors. In selected patients suffering from brain tumors, the invention provide patient an opportunity of possible cure without undergoing a high-risk brain surgery for the removal of brain tumor. Patients suffering from glioma and other types of brain tumors undergo only a minor surgery to make a small hole in cranial bone for placing an indwelling catheter in a brain tumor under CT scan guidance. This treatment can greatly decrease patient mortality, and increase patient survival rate and tumor curability.

The formulation drug of $Na^+$ and $Ca^{2+}$ and treatment methods of the invention can be used as the first-line treatment in patients suffering from thyroid cancer. Such patients can avoid a high-risk surgery or isotopic radiotherapy. This treatment can protect patient from damage to parathyroid glands from surgical procedure. In addition, it can also be used as a preventive cancer treatment in patients who have been planned to have a total thyroidectomy or subtotal thyroidectomy. Prior to surgery, for example, thyroid cancer lesion can be killed in situ by intratumoral injection with the "medicinal ion bomb," and then a "dead thyroid cancer" is safely removed by surgery. This strategy may protect patient from iatrogenic metastasis or intraoperative cancer tissue spreading, and increase patient survival rate and tumor curability.

The formulation drug of $Na^+$ and $Ca^{2+}$ and treatment methods of the invention can be used as the first-line treatment in patients suffering from benign tumors of thyroid glands including, for example, adenoma, thyrophyma, cyst and nodules in thyroid glands.

The formulation drug of $Na^+$ and $Ca^{2+}$ and treatment methods of the invention can be used as the first-line treatment in patients suffering from primary or recurrent hyperthyroidism who can avoid high-risk isotopic radiotherapy or surgery. Prior to treatment, patient takes iodine by mouth. When patient's thyroid glands become small, intrathyroid injection with the "medicinal ion bomb" in both thyroid glands is performed. Patient is simply treated by performing a longitudinal injection in each thyroid gland under ultrasound or CT scan guidance. The mechanism of using the "medicinal ion bomb" in treatment of hyperthyroidism is to reduce the number of thyroid hormone-producing cells as do by surgery and isotopic radiotherapy.

The formulation drug of $Na^+$ and $Ca^{2+}$ and treatment methods of the invention can be used as the first-line treatment in patients suffering from breast cancer. In selected breast cancer patients, the invention provides an opportunity of possible cure using a non-surgical intervention. Such patients can avoid a destructive surgery. The intratumoral injection with the "medicinal ion bomb" in this invention can also be used as a preventive cancer treatment in patients suffering from primary breast cancer who have been considered for lumpectomy or mastectomy or radical mastectomy. Two to 3 days prior to surgery, patient's breast cancer lesion is killed in situ by intratumoral injection with the "medicinal ion bomb," then a "dead breast cancer" is safely removed by surgery. More importantly, it can protect patient from iatrogenic metastasis from surgery, and increase patient survival rate and cancer curability.

The pharmaceutical formulation drug of $Na^+$ and $Ca^{2+}$ and treatment methods of the invention can be used as the first-line treatment in patients suffering from mammary benign diseases including, but not limited to, adenoma, fibroma, fibrocystic change and hyperplasia of breast.

The formulation drug of $Na^+$ and $Ca^{2+}$ and treatment methods of the invention can be used as the first-line treatment in patients suffering from primary prostate cancer. In selected patients, this invention provides an opportunity of possible cure without undergoing conventional hormone therapy, brachytherapy, surgery or chemotherapy that have serious complications, particularly in posttreatment erectile dysfunction and cancer recurrence. The precision-guided intra-prostatic injection with the "medicinal ion bomb" is a minor invasive treatment that doesn't cause the above complications or side effects. Patients can be safely treated through transurethral injection under the guidance of CT scan, ultrasound or cystoscope.

The formulation drug of $Na^+$ and $Ca^{2+}$ and treatment methods of the invention is particularly indicated for patients who suffers from benign prostatic hyperplasia (BPH). In selected patients, this invention provides a unique opportunity to cure BPH without undergoing surgery or hormone therapy.

The formulation drug of $Na^+$ and $Ca^{2+}$ and treatment methods of the invention can be used as the first-line treatment in patients suffering from primary pancreatic cancer. In selected pancreatic cancer patients, this invention provides an opportunity of possible cure of pancreatic cancer without undergoing surgical intervention. Patient's abdominal organs are not damaged if the injection access is selected in the back. Patient is placed the prone position and intratumoral injection with the "medicinal ion bomb" is performed under CT scan guidance.

The formulation drug of $Na^+$ and $Ca^{2+}$ and treatment methods of the invention can be used as a preventive cancer treatment in pancreatic cancer patients who have been considered a surgery. Two to 3 days prior to surgery, a pancreatic cancer lesion is killed in situ by intratumoral injection with the "medicinal ion bomb," then a "dead pancreatic cancer" is safely removed by surgery. This strategy can protect patient from iatrogenic metastasis and increase patient survival rate and cancer curability.

The formulation drug of $Na^+$ and $Ca^{2+}$ and treatment methods of the invention can be used as the first-line treatment in patients suffering from benign tumors of pancreas such as insulinoma, cyst, adenoma and other pancreatic tumors.

The formulation drug of $Na^+$ and $Ca^{2+}$ and treatment methods of the invention can be used as a palliative treatment of pancreatic cancer during a surgery when an advanced stage of pancreatic cancer is un-removable. During laparotomy, the "medicinal ion bomb" solution is injected into pancreatic cancer in direct view. This treatment can relieve patient's cancer condition and improve the life quality of patient.

The formulation drug of $Na^+$ and $Ca^{2+}$ and treatment methods of the invention can be used as the first-line treatment in patients suffering from primary lung cancer, liver cancer and kidney cancer. The treatment is performed under CT scan guidance or direct view during surgery.

The formulation drug of $Na^+$ and $Ca^{2+}$ and treatment methods of the invention can be used as a palliative treatment in patients suffering from colorectal carcinoma and associated with obstruction of large bowel. Under the guidance of endoscope the "medicinal ion bomb" is injected into cancer lesion to relieve obstructive symptoms in emergency.

The formulation drug of $Na^+$ and $Ca^{2+}$ and treatment methods of the invention can be used as the first-line treatment in patients suffering from cervical cancer. The patient is treated by a simple intratumoral injection with the "medicinal ion bomb" in direct view.

The formulation drug of $Na^+$ and $Ca^{2+}$ and treatment methods of the invention can be used as the first-line treatment in patients suffering from pre-malignancy and benign tumors in female and male genital organs.

The formulation drug of $Na^+$ and $Ca^{2+}$ and treatment methods of the invention can be used as the first-line treatment in patients suffering from leiomyoma or leiomyosarcoma in uterus, which can be treated trans-vaginally or under the guidance of peritoneal endoscopy or minor invasive surgery.

The formulation drug of $Na^+$ and $Ca^{2+}$ and treatment methods of the invention can be used as the first-line treatment in patients suffering from benign and malignant tumors of ovary including, but not limited to, ovarian carcinoma, teratoma and fibroid conditions. Patient is treated by placing an indwelling catheter in tumor under the guidance of laparoscopy or minor invasive surgery.

The formulation drug of $Na^+$ and $Ca^{2+}$ and treatment methods of the invention can be used in cosmetic therapy to remove a skin mole, tag, wart and neoplasm in surface of the body.

Taken together, the invention of intratumoral injection with the "medicinal ion bomb" can be used as the first-line treatment of cancer at least in the nine human organs (skin and subcutaneous tissue, brain, thyroid, breast, lung, liver, pancreas, prostate, and genital organs) and four category benign diseases (skin and subcutaneous neoplasm, breast fibrocystic changes, benign prostatic hyperplasia and thyroid nodules).

EXAMPLES

This invention is more specifically illustrated by the following representative examples of the procedure of intratumoral injection with the "medicinal ion bomb" in animal tumors and human cancer conditions.

The formula of the "medicinal ion bomb" comprises five pharmaceutical compositions of 5.0479 M of $Na^+$, 250 mM of $Ca^{2+}$, 20mg of adrenaline, 10ml of Ultravist 370 and appropriate amount of distilled water, that are in order mixed to make the final volume of one liter of saturated solution at room temperature.

$Na^+$ and $Ca^{2+}$ in the formulation make up the killing powers, adrenaline is a vasoconstrictor for contracting tumor vessels to make an "artificial tumor capsule" in a non-capsuled cancer or tumor. Ultravist 370 is an X-ray contrast medium for tracking diffusion of the "medicinal ion bomb" inside a cancer or tumor to be treated. Distilled water is the dissolvent, and Studies have confirmed that the formulation of the "medicinal ion bomb" solution using 5.0479 M of $Na^+$ and 250 mM of $Ca^{2+}$ at room temperature is a completely dissolved.

The treatment method of intratumoral injection with the "medicinal ion bomb" solution in the invention has claimed that the route of administration of the "medicinal ion bomb" solution is through intratumoral injection (direct injection) of the "medicinal ion bomb" solution into a cancer or tumor in a subject.

In addition, minimal and maximal effective treatment concentrations of $Na^+$ and $Ca^{2+}$ for intratumoral injection have been claimed. When $Na^+$ are used alone or in combination with other compositions for intratumoral injection, the effective treatment concentration of $Na^+$ ranges from 2.0 M to about 5.4414 M at room temperature. When $Ca^{2+}$ are used alone or in combination for intratumoral injection, the effective treatment concentration of $Ca^{2+}$ ranges from about 50 mM to 6.0 M at room temperature.

Example 1

FIG. 1. A MCA207 mouse sarcoma model in C57BL6 mouse. FIG. 1A. A pretreatment tumor was 8mm×8mm in size. FIG. 1B. The standard procedure of intratumoral injection with the "medicinal ion bomb" in mouse. FIG. 1C. The mouse sarcoma was killed by a single injection with 0.10ml of the "medicinal ion bomb."

Example 2

Figure 2:
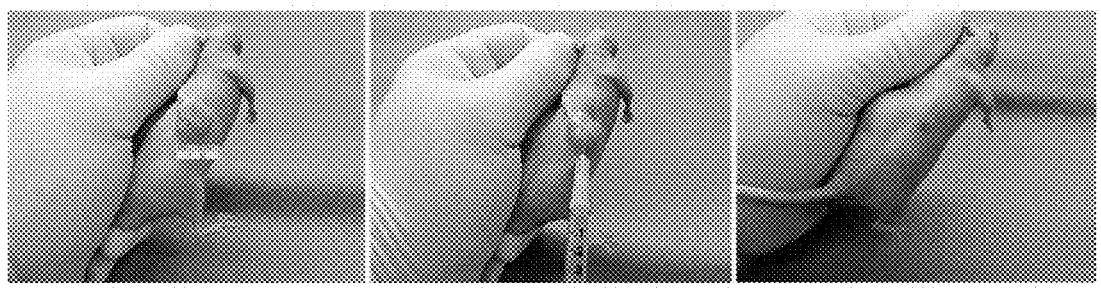
FIG. 2. A MCF7 human breast cancer model in nude mouse.

FIG. 2. A MCF7 human breast cancer model in nude mouse. FIG. 2A. A pretreatment human breast cancer 13mm×13mm in size that is equal to 3%±body weight of the mouse. FIG. 2B. The standard procedure of intratumoral injection with the "medicinal ion bomb" in mouse. FIG. 2C. The cancer was killed by a single intratumoral injection with 0.14ml of the "medicinal ion bomb."

Example 3

Figure 3:
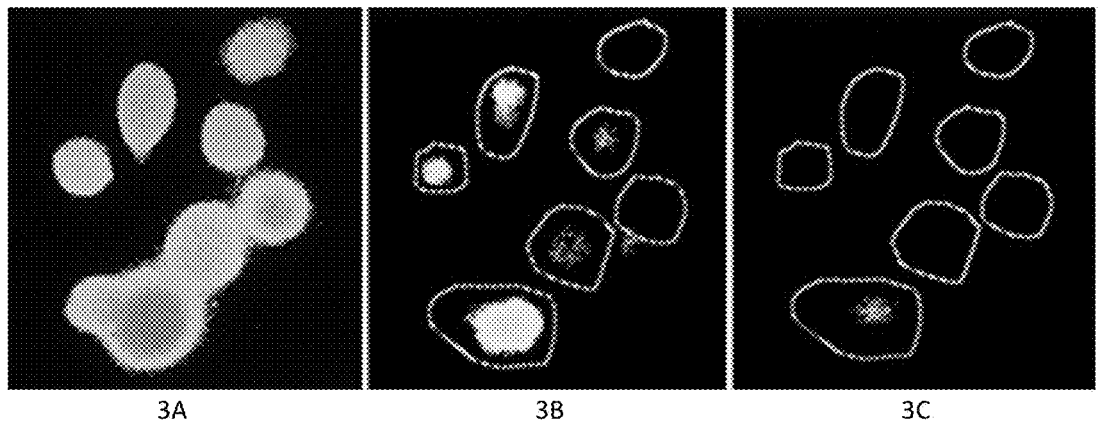
FIG. 3. The use of the fluorescent labeled $Ca^{2+}$ probe technique in ex vivo determination of the influx of $Ca^{2+}$ from the extracellular fluid into intracellular fluid in MCF7 human breast cancer cells.

FIG. 3. The use of fluorescent $Ca^{2+}$ probe technique in ex vivo determination of the influx of $Ca^{2+}$ from the extracellular fluid into intracellular fluid in MCF7 human breast cancer cells. FIG. 3A. Seven pretreatment cancer cells using the fluorescent labeled $Ca^{2+}$ probes. FIG. 3B. Two of 7 cancer cells were killed by the "medicinal ion bomb" in 14±seconds after starting treatment. FIG. 3C. All 7 cancer cells were killed in 18±seconds after starting treatment. The procedure of measuring the influx of $Na^+$ was the same as the abovementioned but using the fluorescent $Na^+$ probe.

Example 4

Figure 4:
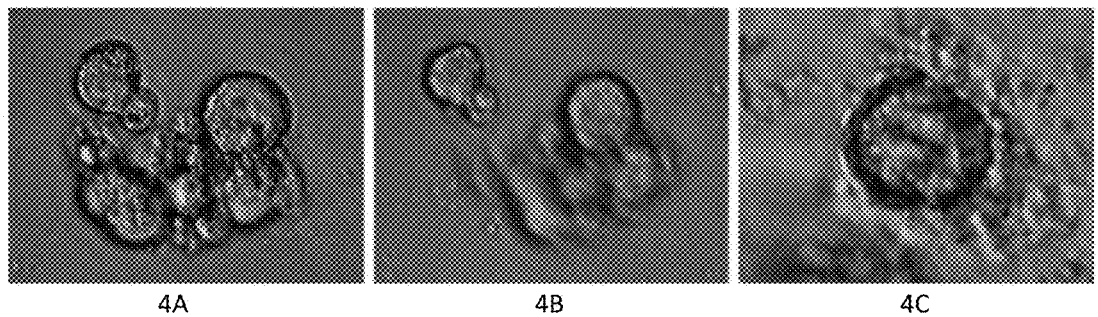
FIG. 4. Micrographs of 3 videos images of the Nikon Diaphot inverted microscope.

FIG. 4. Micrographs of video images of the Nikon Diaphot inverted microscope. FIG. 4A. Pretreatment MCF7 human breast cancer cells as the self-control. In FIG. 4B. Cancer cells treated were experiencing a vortex-like rotation in tissue culture in 5±seconds after adding the "medicinal ion bomb." FIG. 4C. All cancer cells were killed in 16±seconds after starting treatment. Cancer cells in these 3 micrographs were from the same field. Magnification ×400.

Example 5

Figure 5:
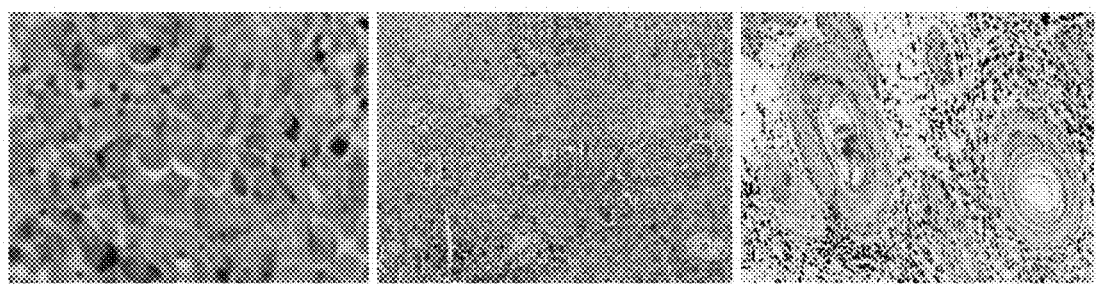
FIG. 5 shows a group of micrographs to describe pathologic features of in vivo MCA207 mouse sarcoma treated with the "medicinal ion bomb.

FIG. 5 shows a group of micrographs to describe pathologic features of in vivo MCA207 mouse sarcoma treated with the "medicinal ion bomb." FIG. 5A. White lines surrounding cancer cells were sodium ions (salts) and calcium ions (salts) in the cancer tissue in mouse. Magnification ×1000. FIG. 5B. The cancer tissues treated were necrotic where the "medicinal ion bomb" reached. Magnification ×400. FIG. 5C. Multiple thrombi in a treated tumor section. Magnification ×400.

Example 6

Figure 6:
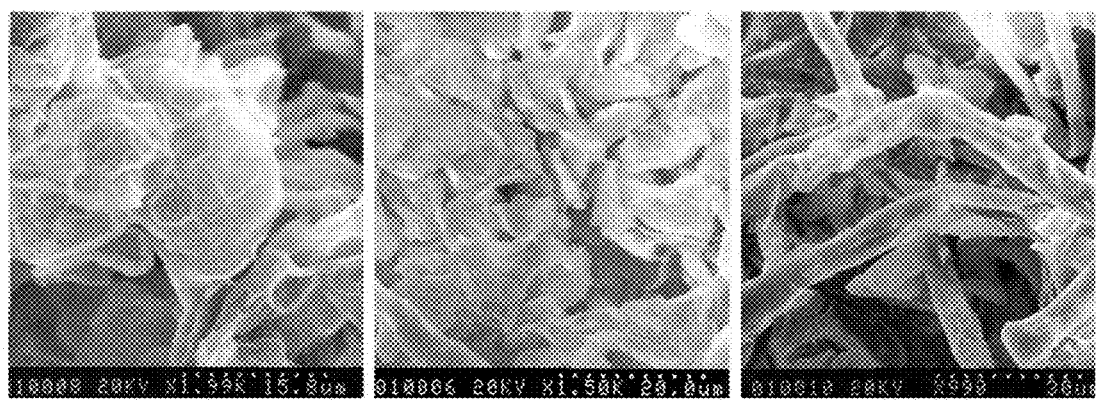
FIG. 6. A group of micrographs of scanning electron microscope (SEM) of MCF7 human breast cancer models in nude mice.

FIG. 6. A group of micrographs of SEM of MCF7 human breast cancer models in nude mice. FIG. 6A. Control cancer cells. FIG. 6B. Membranes of cancer cells treated were broken into debris. Severely injured tumor blood vessels, particularly damages to the outer layer structure of arterioles and venules in tumor tissue. Multiple tumor vessels were broken down.

Example 7

Figure 7:
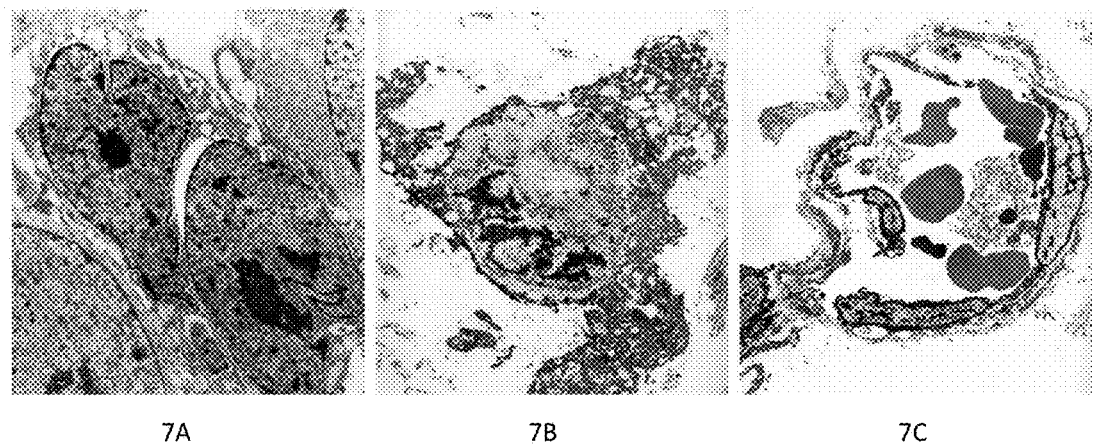
FIG. 7. A group of micrographs of transmission electron microscope (TEM) of MCF7 human breast cancer models in nude mice.

FIG. 7. A group of micrographs of TEM of MCF7 human breast cancer models in nude mice. FIG. 7A. Control cancer cells. FIG. 7B. Membrane, cytoskeleton, mitochondria, lysosome, nucleus and other organelles of a cancer cell were targeted and damaged by the "medicinal ion bomb." FIG. 7C. Completely damaged outer layer, median layer and inner layer of a tumor vessel. An endothelial cell in the inner lumen of an arteriole was coming off. Magnifications ×2000.

Example 8

Figure 8:
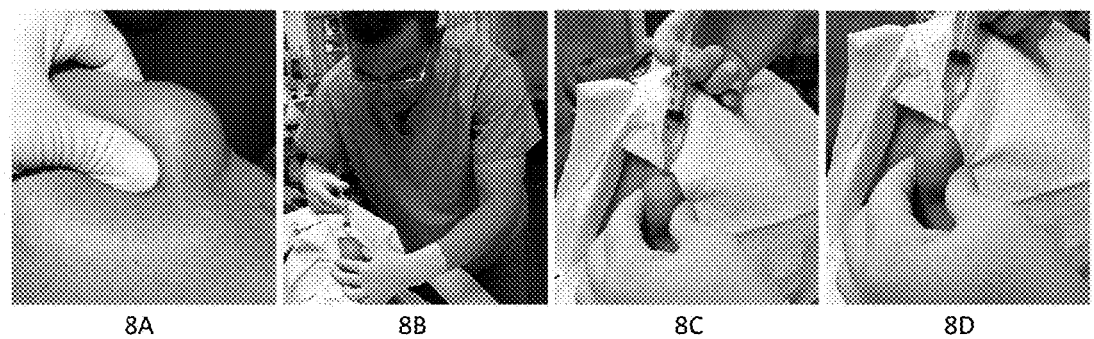
FIG. 8. A clinical doctor was performing an intratumoral injection with the "medicinal ion bomb" in a patient who suffered from a large benign tumor.

FIG. 8. A clinical doctor was performing an intratumoral injection with the "medicinal ion bomb" in a patient who suffered from a large benign tumor. FIG. 8A. A pretreatment tumor at 40mm×60mm in size in the patient's right shoulder. FIG. 8B. A pressure intratumoral injection with 3ml of the "medicinal ion bomb" to the tumor. FIG. 8C. The opening of the needle was upward. FIG. 8D. The opening of the needle was downward.

Example 9

Figure 9:
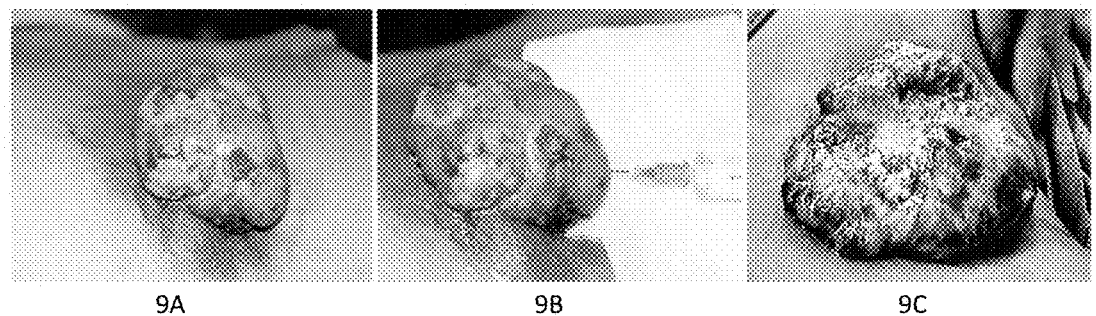
FIG. 9. The case of an 82 year-old lady suffered from a huge squamous cell carcinoma in the lower back for 3 years.

FIG. 9. The case of an 82 year-old lady who suffered from a huge squamous cell carcinoma in the lower back for 3 years. FIG. 9A. The pretreatment carcinoma was 70mm×70mm in size. FIG. 9B. A single intratumoral injection with 26ml of the "medicinal ion bomb" was administered into the cancer lesion. FIG. 9C. This was a counterpart photo of the video image 5 after treatment. Macroscopically, the entire cancer lesion treated was completely dead. Microscopically, all cancer tissue was necrotic.

Example 10

Figure 10:
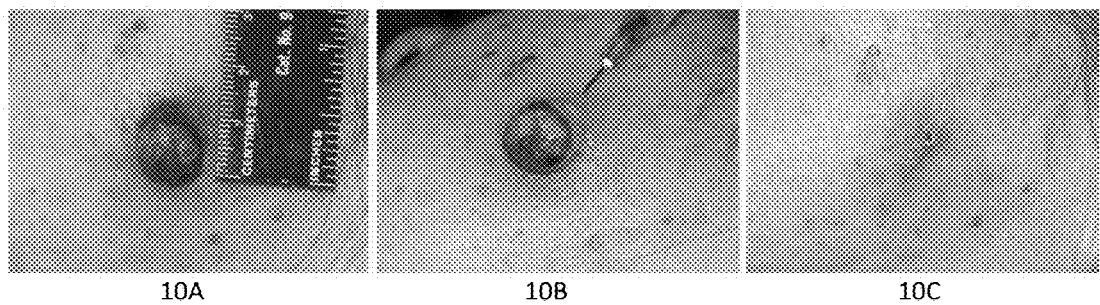
FIG. 10 The case of a 70 year-old lady suffered from a squamous cell carcinoma in the left face.

FIG. 10. The case of a 70 year-old lady suffered from a squamous cell carcinoma in the left face. FIG. 10A. The pretreatment cancer was 15mm×15mm in size. The cancer was killed by one single intratumoral injection with 1.0ml of the "medicinal ion bomb." FIG. 10B. The standard procedure of intratumoral injection with the "medicinal ion bomb" in human patient. FIG. 10C. Seven days after treatment, the cancer lesion developed coagulative necrosis that looked like a charred dead cancer remainder. The wound was healed without scar or defect by 2 weeks. A 3 year follow-up study showed no recurrence of the treated cancer.

Example 11

Figure 11:
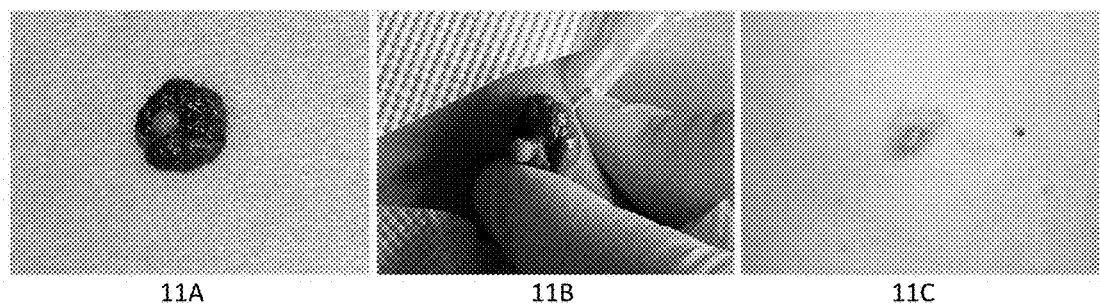
FIG. 11. The case of a 52 year-old lady suffered from a skin malignant tumor. It was an uncommon tumor that had a second tumor (brown) grown from its parental tumor (black).

FIG. 11. The case of a 52 year-old lady who suffered from a skin malignant tumor. It was an uncommon tumor that had a second tumor (brown) grown from its parental tumor (black). FIG. 11A. The pretreatment tumor at 20mm×20mm in size. FIG. 11B. The standard procedure of intratumoral injection with the "medicinal ion bomb" in human patient. FIG. 11C. Two tumors were killed by a single intratumoral injection with 0.5ml of the "medicinal ion bomb" in 3 days, and the wound was healed by 2 weeks after treatment. A 3 year follow-up study showed no relapse of the tumor.

Example 12

Figure 12:
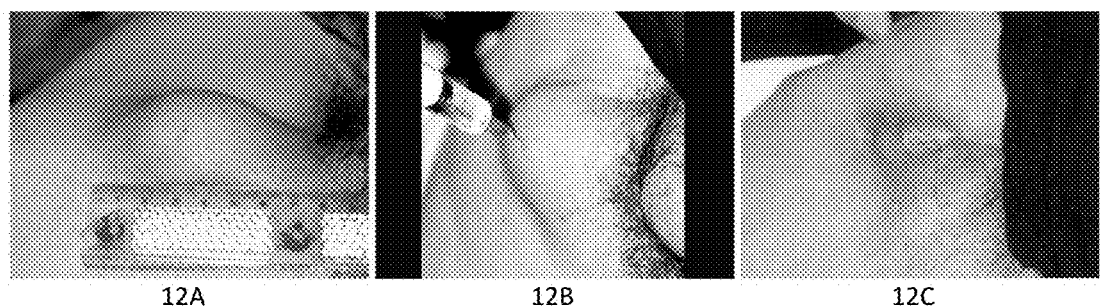
FIG. 12. The case of a 74 year-old man suffered from a metastatic cancer in the left inguinal area from the penis.

FIG. 12. The case of a 74 year-old man who suffered from a metastatic cancer in the left inguinal area from the penis. FIG. 12A. The pretreatment cancer at 50mm×70mm in size. FIG. 12B. The cancer lesion was treated by one single intratumoral injection with 3.5ml of the "medicinal ion bomb." FIG. 12C. The cancer was killed by 4 days and the wound was healed by 3 weeks.

Example 13

Figure 13:
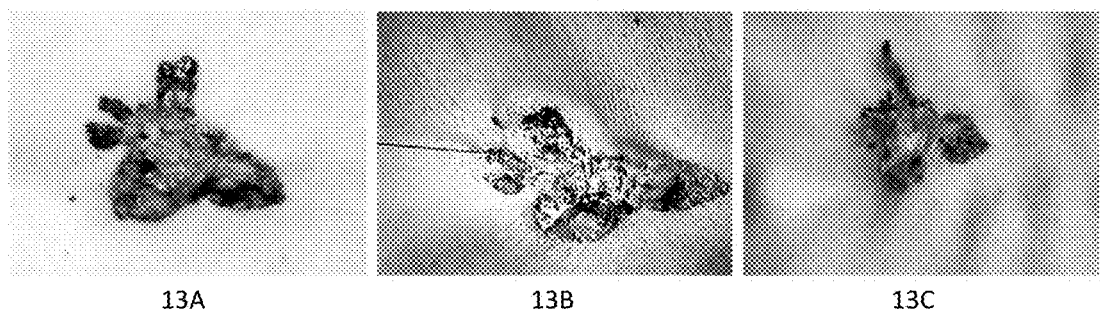
FIG. 13. The case of an 82 year-old man suffered from melanoma in the front chest for 2 years.

FIG. 13. The case of an 82 year-old man who suffered from melanoma in the front chest for 2 years. FIG. 13A. A typical pretreatment butterfly-pattern melanoma in a human patient. FIG. 13B. A counterpart photo of the video image to demonstrate a single intratumoral injection with 1.2ml of the "medicinal ion bomb" into the melanoma. FIG. 13C. The melanoma was killed in days and the wound was healed by 3 weeks after treatment. A 9 year follow-up study showed no recurrence of the melanoma.

Example 14

Figure 14:
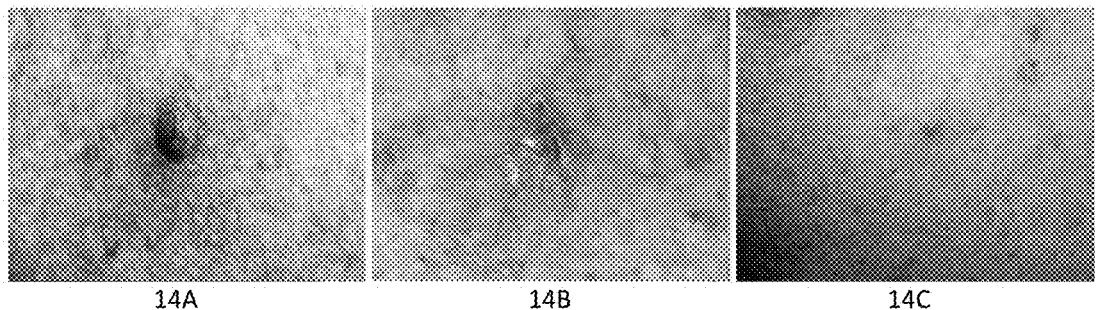
FIG. 14. The case of a 58 year-old man suffered from basal cell carcinoma in the front chest.

FIG. 14. The case of a 58 year-old man suffered from basal cell carcinoma in the front chest. FIG. 14A. A pretreatment basal cell carcinoma at 12mm×12mm in size. FIG. 14B. The carcinoma regressed one week after a single intratumoral injection with 0.5ml of the "medicinal ion bomb." FIG. 14C. The site of the carcinoma regressed was healed by 3 weeks after treatment. An 8 year follow-up study showed no recurrence of the carcinoma.

Example 15

Figure 15:
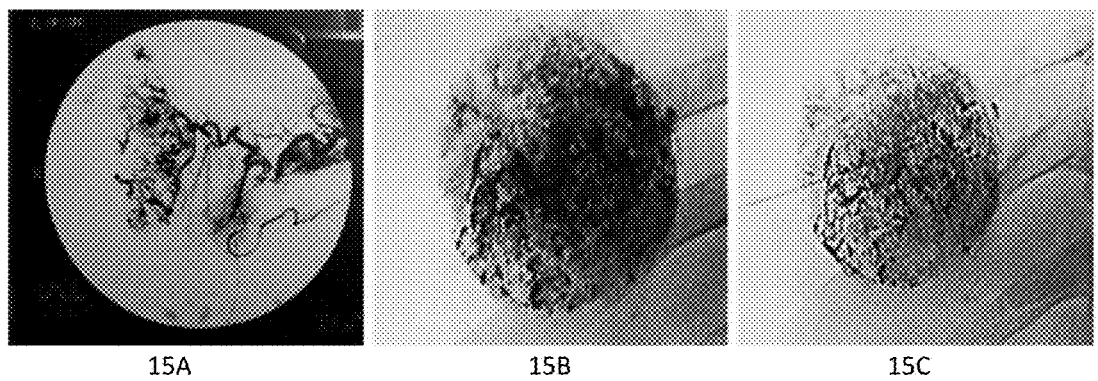
FIG. 15A. An image of angiography through hepatic artery that showed a large liver cancer in the right lobe of the liver in a 62 year-old man.
FIG. 15B. The image of a large liver cancer before treatment from the same patient. An extra-length indwelling catheter was placed in the center of liver cancer lesion and 20ml of the "medicinal ion bomb" was administered.
FIG. 15C. Seven days after treatment the liver cancer lesion became smaller from the pretreatment size at 67mm×67mm×80mm to posttreatment size at 45mm×45mm×60mm.

FIG. 15A. An image of angiography through hepatic artery showed a large liver cancer in the right lobe of the liver in a 62 year-old man. FIG. 15B. The image of a large liver cancer before treatment from the same patient. An indwelling extra-length catheter needle was placed in the center of liver cancer lesion and 20ml of the "medicinal ion bomb" was administered. FIG. 15C. Seven days after treatment the liver cancer lesion became smaller from the pretreatment size at 67mm×67mm×80mm to posttreatment size 45mm×45mm×60mm.

Example 16

Figure 16:
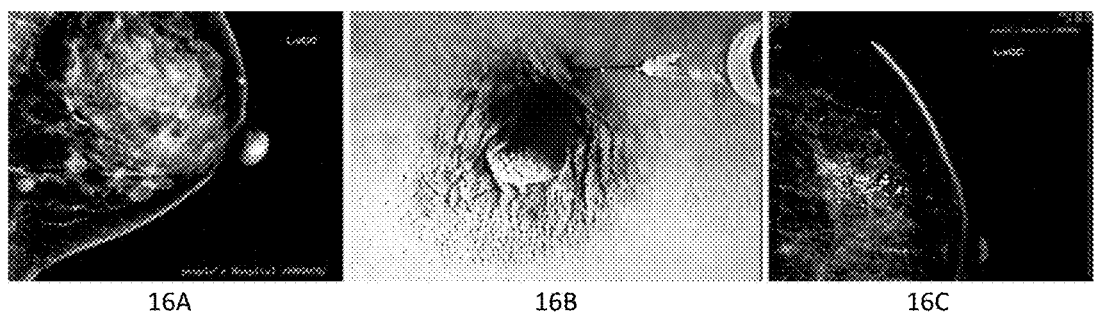
FIG. 16. The case of a lady who suffered from breast fibrocystic changes.

FIG. 16. The case of a lady who suffered from breast fibrocystic changes. FIG. 16A. An image of pretreatment mammography showed a large cyst at 40mm×40mm in size behind of the left nipple. Several small fibrocystic lesions were surrounding the large cyst. FIG. 16B. The mucous fluid inside cyst was sucked, and the large cyst was repeatedly washed and sucked using the "medicinal ion bomb" solution. Then a single intra-cystic injection with 3.5ml of the "medicinal ion bomb" was given. FIG. 16C. The image of posttreatment mammography demonstrated the breast fibrocystic disease was cured 3 months after treatment.

Example 17

Figure 17:
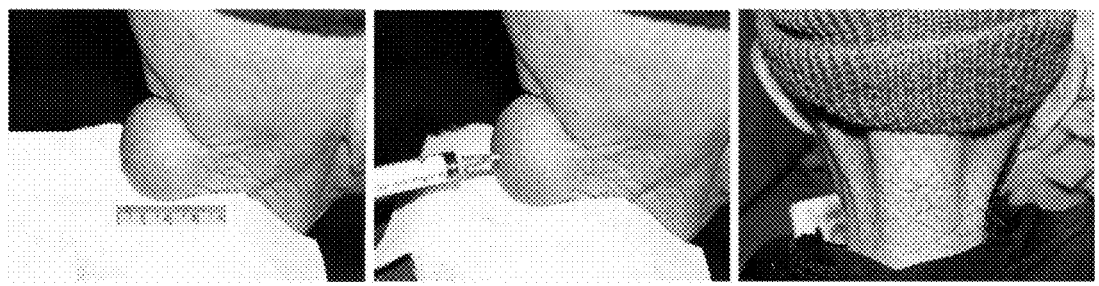
FIG. 17. The case of a 78 year-old man suffered from lipoma. The tumor was located in his rear neck for 18 years.

FIG. 17. The case of a 78 year-old man suffered from lipoma. The tumor was located in his rear neck for 18 years. FIG. 17A. The pretreatment tumor was 40mm×40mm in size. FIG. 17B. A single intratumoral injection with 2.0ml of the "medicinal ion bomb" was administered into the tumor. FIG. 17C. The tumor was cured by 8 weeks. A 9 year follow-up study showed no recurrence of the treated tumor.

Example 18

Figure 18:
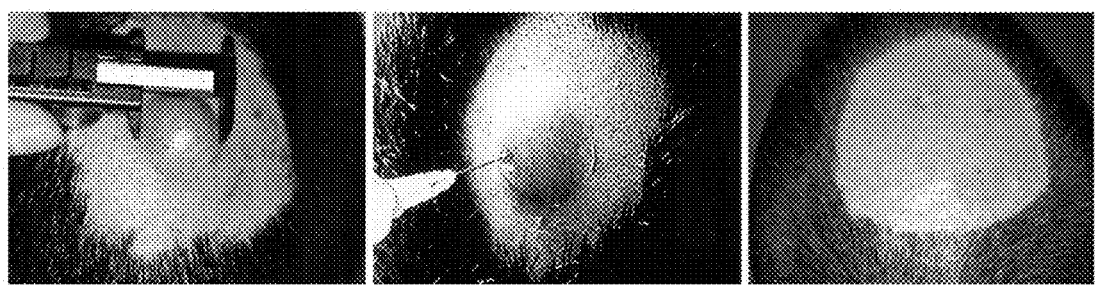
FIG. 18. The case of a patient who suffered from atheroma.

FIG. 18. The case of a patient suffered from atheroma. FIG. 18A. A pretreatment atheroma in the vertex at 18mm×18mm in size. FIG. 18B. A counterpart photo of the video image showed a single intratumoral injection with 0.5ml of the "medicinal ion bomb." FIG. 18C. The atheroma was cured. This photo was taken when a 9 year follow-up study was performed.

Example 19

Figure 19:
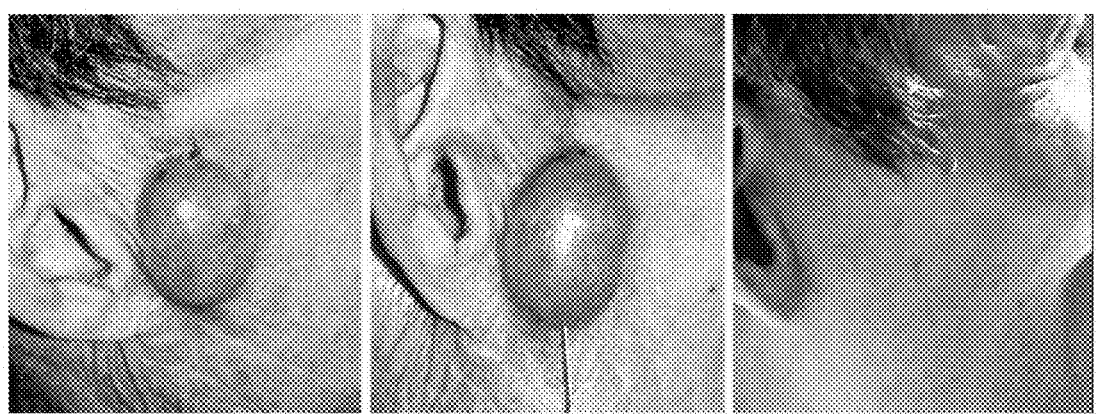
FIG. 19A. The case of a 66 year-old man suffered from an atheroma at 22mm×28mm in size.
FIG. 19B. The tumor was treated by a single intratumoral injection with 1.5ml of the "medicinal ion bomb.
" FIG. 19C. A 9 year follow-up study showed no recurrence of the tumor.

FIG. 19A. The case of a 66 year-old man suffered from an atheroma at 22mm×28mm in size. FIG. 19B. The tumor was treated using a single intratumoral injection with 1.5ml of the "medicinal ion bomb." FIG. 19C. A 9 year follow-up study showed no recurrence of the tumor.

Example 20

Figure 20:
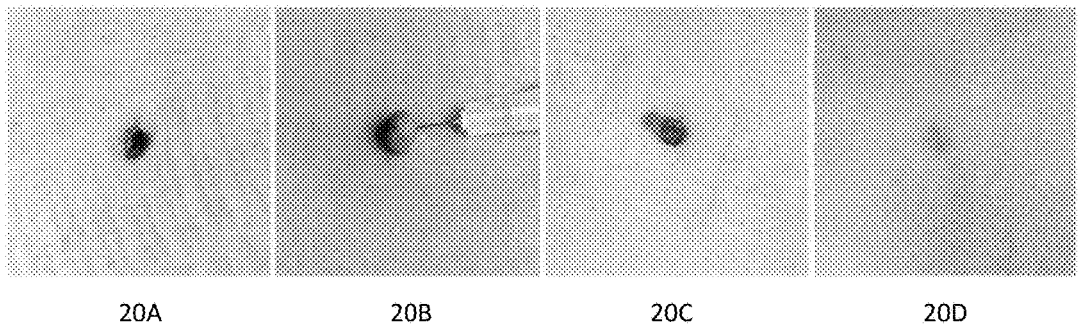
FIG. 20. The application of intralesional injection with the "medicinal ion bomb" in cosmetic conditions.

FIG. 20. The application of intralesional injection with the "medicinal ion bomb" in cosmetic conditions. FIG. 20A was a skin mole in the patient. FIG. 20B. A single intralesional injection with 0.2ml of the "medicinal ion bomb" was given. FIG. 20C. The mole developed coagulative necrosis by 7 days posttreatment. FIG. 20D. The skin mole was removed without scar or defect.

Supplemental Examples and Materials

Preparations of the "Medicinal Ion Bomb" and the "Medicinal Ion Bomb" Solution

The formulation cancer drug of the "medicinal ion bomb" comprises 5.0479 of $Na^+$ (pharmaceutical NaCl, molecular weight 58.44), 250 mM of $Ca^{2+}$ (pharmaceutical $CaCl_2$, molecular weight 111), 20mg of adrenaline, 10ml of Ultravist 370 and an appropriate amount of distilled water that are in order mixed to make one liter of injection at room temperature. The "medicinal ion bomb" injection is bottled in glass ampoules at volumes of 5.0ml, 10ml, and 20ml. They are pasteurized and packed in a designed treatment kit.

Solubility of the "Medicinal Ion Bomb"

The compositions of the "medicinal ion bomb" comprise 5.0479 M of NaCl and 250 mM of $CaCl_2$ that are completely dissolved in about 890ml of distilled water at room temperature by 7 minutes, making the final volume of one liter of the "medicinal ion bomb" solution (the saturated ionic solution).

The "Medicinal Ion Bomb" and the "Medicinal Ion Bomb" Solution

The "medicinal ion bomb" for cancer treatment in this study project can be made in two forms. One is in the form of powders of NaCl and $CaCl_2$ that is called the "medicinal ion bomb"; and the other one is in the form of liquid that is termed the "medicinal ion bomb" injection. Generally, the terms of the "medicinal ion bomb" and the "medicinal ion bomb" solution in this study project can be interchangeable.

Intratumoral Injection and Precision-Guided Intratumoral Injection with the "Medicinal Ion Bomb"

When the "medicinal ion bomb" injection is used to treat a tumor or cancer in surface of the body, skin, or subcutaneous tissue, the treatment is performed under direct view that is termed intratumoral injection with the "medicinal ion bomb." When a tumor or cancer is located in deep tissue or internal organ, the treatment is accurately performed by means of CT scan guidance or ultrasound guidance that is termed the precision-guided intratumoral injection with the "medicinal ion bomb."

In Vivo Toxicity of $Na^+$, $K^+$, $Ca^{2+}$ and $Mg^{2+}$

At the beginning, in vivo toxicity of high concentrations of $Na^+$, $Ca^{2+}$, $K^+$, and $Mg^{2+}$ in BALB/c mice was examined. Here, the model of intramuscular injection using 35% NaCl, 35% $CaCl_2$, 34% KCl and 35% $MgCl_2$ (each solution contains 20mg of adrenaline/liter as its dose in the "medicinal ion bomb" solution) represent the model of intratumoral injection with the above 4 types of ionic solutions.

BALB/c mice were housed and inbreeded in the contracted university animal facilities that was in accordance with the NIH regulation. Body weight of the BALB/c mice at the experiment was 30±g. The toxicity test was performed using intramuscular injection with 0.2ml of 35% NaCl, 35% $CaCl_2$, 34% KCl or 35% $MgCl_2$ in a mouse, respectively.

In total, 20 BALB/c mice (10 males and 10 females) were randomly divided into 5 groups, with 4 mice in each group. Animals in group 1 received intramuscular injection with 0.2ml of 35% NaCl and survived the experiment, indicating that the dose of intramuscular injection with 0.2ml of 35% NaCl solution is safe in mouse weighing 30g.

Animals in group 2 received intramuscular injection with 0.2ml of 35% $CaCl_2$ and died in 3 hours after treatment, indicating that high dose of $CaCl_2$ was toxic.

Animals in group 3 received intramuscular injection with 0.2ml of 17.5% $CaCl_2$ and survived the experiment, indicating that intramuscular injection with low dose of $CaCl_2$ was safe.

Animals in group 4 received intramuscular injection with 0.2ml of 34% KCl and died from cardiopulmonary failure 3 hours after treatment, indicating that high concentration of KCL was toxic, that cannot be used to be an component in the formula of the "medicinal ion bomb".

Animals in group 5 received intramuscular injection with 0.2ml of 35% $MgCl_2$ that was not well absorbed. It was given up.

Ex Vivo Killing Action of the "Medicinal Ion Bomb" to 18 Types of Human Cancer Cell Lines The role of the "medicinal ion bomb" in killing cancer cells was tested in tissue culture. Cancer cells were seeded in Petri dish using DMEM or RPMI1640 medium supplemented with 10% FCS. Each type of cancer cell line was prepared at $2 \times 10^6$ cells/ml in a 5ml plastic tube. The supernant was removed by centrifugation and then 1.0ml of the "medicinal ion bomb" solution was added to each tube. Three to five minutes later, 0.5% Trypan Blue was added and mixed with the cell suspension for 2 minutes. The number of dead cancer cells was counted under an inverted microscope. Selected samples of treated cancer cell suspension for flow cytometer were prepared in phosphate-buffered saline (PBS) and mortality of cells was assayed using flow cytometer (Beckman Coulter Inc., CA).

This experiment included one control group in which cancer cells were treated with normal saline, and the other 18 types of human cancer cell lines were treated with the "medicinal ion bomb" solution. The data showed that no cancer cells were dead in the control group. However, all 18 types of human cancer cell lines were killed by the "medicinal ion bomb" solution in 3 to 30 minutes, including A549 human lung cancer, ARO human thyroid cancer, CWR-22 human prostate cancer, HeLa human cervical cancer, HL60 human leukemia, HT-29 human colorectal cancer, Jurkat human T cell leukemia, K562 human leukemia, M2 human lymphoma, M24 Human melanoma, LNCaP human prostate cancer, MCF7 human breast cancer, MDA-MB-231 human breast adenocarcinoma, OVCAR3 human ovary cancer, PC3 human prostate cancer, SK-RC-52 human kidney cancer, T-47D human breast epithelial tumor, and U87 human glioblastoma.

Intratumoral Injection LD50 of the "Medicinal Ion Bomb" Solution in Mouse

In toxicology, the median lethal dose ($LD_{50}$) of a toxin, radiation, or pathogen is the dose required to kill half the members of a tested population after a specified test duration. $LD_{50}$ figures are frequently used as a general indicator of a substance's acute toxicity. Experimental data of the invention have showed that the $LD_{50}$ of the "medicinal ion bomb" for intratumoral injection was 7.5ml/kilogram (kg) in mouse.

Before conducting the experimentation of the $LD_{50}$ in this study, over hundreds of nude mice bearing tumor underwent intratumoral injection with the "medicinal ion bomb." The experience from experimental observation showed that the $LD_{50}$ of the "medicinal ion bomb" for intratumoral injection was 0.15±ml in a nude mouse weighing 30g.

In this group, 12 nude mice bearing MCF7 human breast cancer were tested. Each nude mouse was subcutaneously inoculated with a MCF7 human breast cancer. The experiment started, when tumors reached 8mm×8mm in size, with an injection of 0.15ml of the "medicinal ion bomb" solution to the tumor. The time and number of animal death and survival, tumor size, and samples for pathology were collected for statistical analysis.

$NaCl$ and $CaCl_2$ are not generally considered poisonous. Data have confirmed that the intratumoral injection $LD_{50}$ of the "medicinal ion bomb" was 7.5ml/kilogram (kg) in mouse. According to Pharmacology and Toxicology, Guidance for Industry: Estimating the maximum safe starting dose in initial clinical trials for therapeutics in adult healthy volunteers. FDA, Jul. 2005, because the conversion factor of mouse drug dose to human equivalent dose (HED) was 0.081, the intratumoral injection $LD_{50}$ of the "medicinal ion bomb" solution in human is calculated by:

7.5ml/kg mouse drug dose ×0.081=0.607.5ml/kg (HED)
=179.213mg/kg NaCl+16.86mg/kg $CaCl_2$ (HED)

The data of the invention confirmed that the intratumoral injection $LD_{50}$ of the "medicinal ion bomb" solution" in nude mouse weighing 20±grams is 0.15 ml. Shown below are the calculation steps of intratumoral injection $LD_{50}$ of the "medicinal ion bomb" solution from mouse drug dose to HED.

Intratumoral Injection LD50 of the "Medicinal Ion Bomb" Solution in Mouse is Calculated by Average body weight of nude mice≈20g.
1.0kg=1,000g.
1,000g/20g=50 folds.
Intratumoral injection $LD_{50}$ of the "medicinal ion bomb" solution in a nude mouse is 0.15ml.
0.15ml×50 folds=7.5ml/kg "medicinal ion bomb" solution in mouse.
7.5ml/kg×295=2212.5mg/kg NaCl in mouse $LD_{50}$.
Here the 295 means 295g of NaCl in one liter of the "medicinal ion bomb" solution.
7.5ml/kg×27.75=208.125mg/kg $CaCl_2$ in mouse $LD_{50}$.
Here the 27.75 means 27.75g of $CaCl_2$ in one liter of the "medicinal ion bomb" solution.
Intratumoral injection $LD_{50}$ of the "medicinal ion bomb" solution in nude mouse
is 7.5ml/kg body weight or
=2212.5mg/kg NaCl+208.125mg/kg $CaCl_2$.

Intratumoral Injection LD50 of the "medicinal ion bomb" solution in Human is Calculated by Intratumoral injection $LD_{50}$ of the "medicinal ion bomb" solution in mouse is 7.5ml/kg body weight.
Here 0.081 is the conversion factor of mouse drug dose in mg/kg to HED in mg/kg.
7.5ml×0.081=0.6075ml/kg "medicinal ion bomb" solution in HED.
0.6075ml/kg×295=179.213mg/kg NaCl in HED.
Here the 295 means 295g of NaCl in in one liter of the "medicinal ion bomb" solution.
0.6075ml/kg×27.75=16.86mg/kg $CaCl_2$ in HED.
Here the 27.75 means 27.75g of $CaCl_2$ in one liter of the "medicinal ion bomb" solution.
Intratumoral injection $LD_{50}$ of the "medicinal ion bomb" solution in human
is 0.6075ml/kg body weight or
=179.213mg/kg NaCl+16.86mg/kg $CaCl_2$.

Intratumoral Injection MTD of the "Medicinal Ion Bomb" Solution in Mouse

Maximum tolerated dose (MTD) refers to the highest dose of a radiological or pharmacological treatment that will produce the desired effect without unacceptable toxicity. The experimental data of the invention have confirmed that the intratumoral injection MTD of the "medicinal ion bomb" solution was 7.0ml/kg in mouse.

In this group, 15 nude mice bearing MCF7 human breast cancer were divided into 5 groups with 3 animals in each subgroup. Animals in subgroup-1 received intratumoral injection with 0.15ml of the normal saline as the control. Animals in subgroup-2 received intratumoral injection with 0.12ml of the "medicinal ion bomb" solution. Animals in subgroup-3 received intratumoral injection with 0.13ml of the "medicinal ion bomb" solution. Animals in subgroup-4 received intratumoral injection with 0.14ml of the "medicinal ion bomb" solution. And animals in subgroup-5 received intratumoral injection with 0.15ml of the "medicinal ion bomb" solution. Each nude mouse was subcutaneously inoculated with a MCF7 human breast cancer. The experiment started, upon tumor growth at 8mm×8mm in size. The experimental data of the invention have confirmed that the intratumoral injection MTD of the "medicinal ion bomb" solution in nude mouse weighing 20g was 0.14ml or 75ml/kg) in mice.

Shown below are the calculation steps of the intratumoral injection MTD of the "medicinal ion bomb" solution from mouse to human.

Average body weight of nude mice≈20g.
1.0kg=1,000g.
1,000g/20 g=50 folds.
Intratumoral injection MTD of the "medicinal ion bomb" solution is 0.14ml in a nude mouse.
0.14ml×50 folds=7.0ml/kg of the "medicinal ion bomb" solution in mouse.
Here 0.081 is the conversion factor of mouse drug dose in mg/kg to HED in mg/kg.
7.0ml×0.081=0.567ml/kg "medicinal ion bomb" solution in human.
0.567ml/kg×295=167.265mg/kg NaCl in human.
Here the 295 means 295g of NaCl in one liter of the "medicinal ion bomb" solution.
0.567ml/kg×27.75=15.734mg/kg $CaCl_2$ in human.
Here the 27.75 means 27.75g of $CaCl_2$ in one liter of the "medicinal ion bomb" solution.

The intratumoral injection MTD of the "medicinal ion bomb" solution is 7.0ml/kg in mouse, the conversion factor of mouse drug dose to HED is 0.081. Here the intratumoral injection MTD of the "medicinal ion bomb" in human is calculated by:

7.0ml/kg mouse drug dose×0.081=0.567ml/kg in HED=167.265mg/kg NaCl+15.734mg/kg $CaCl_2$ in HED Tumor Size, Tumor Weight, Blood Volume and Volume of "Medicinal Ion Bomb" Solution As described previously, we conducted ex vivo experiments of diffusion of the "medicinal ion bomb" solution in beef liver, in vivo experiments of diffusion of the "medicinal ion bomb" in the liver of living rats and rabbits. According to human physiology, blood volume is about 80ml/kg body weight in adult. The data showed that a tumor at 25mm×25mm×30mm in human patient was killed by about 1.0ml of the "medicinal ion bomb" solution. A solid tumor was at 45mm×6mm in size in human patient that was killed by approximately 5.0ml to 6.0ml of the "medicinal ion bomb" solution. Further, a solid tumor at 7mm×8mm in size that was killed by about 30ml of the "medicinal ion bomb" solution. The estimated volume of the "medicinal ion bomb" in different sizes of tumor is calculated in Table 1 below.

TABLE 2

Calculation of the Required Volume of the "Medicinal Ion Bomb" in Different Sizes of Tumor

| Tumor Size | Tumor Weight (g) | Blood Volume (80 mL/kg) | Ion Bomb Solution Needed (mL) |
|---|---|---|---|
| 1 cm × 1 cm × 1 cm | 1.25 | 0.12 | 0.12-0.15 |
| 2 cm × 2 cm × 2 cm | 8.6 | 0.69 | 0.5-1.0 |
| 3 cm × 3 cm × 3 cm | 28 | 2.24 | 1.0-2.0 |
| 4 cm × 4 cm × 4 cm | 55 | 4.4 | 2.0-3.0 |
| 5 cm × 5 cm × 5 cm | 162 | 13 | 5.0-10 |
| 6 cm × 6 cm × 6 cm | 255 | 20.4 | 10-20 |
| 7 cm × 7 cm × 7 cm | 420 | 33.6 | 30-40 |
| 8 cm × 8 cm × 8 cm | 590 | 47.2 | 40-50 |
| 9 cm × 9 cm × 9 cm | 726 | 54.1 | 50-60 |
| 10 cm × 10 cm × 10 cm | 1,150 | 80 | 60-80 |

Table 1 shows three repeated measurements of ex vivo tumor size and tumor weight that were examined using fresh en bloc pork meats. The calculation of blood volume in tumor tissue is cited from the Oxford Food & Nutrition Dictionary in which the average blood volume is 5.3 L (78ml/kg body weight) in male and 3.8 L (56ml/kg body weight) in female. Here, the constant "80ml" of blood volume per kg body weight is used to estimate blood volume in different sizes of tumor.

Figure 21:
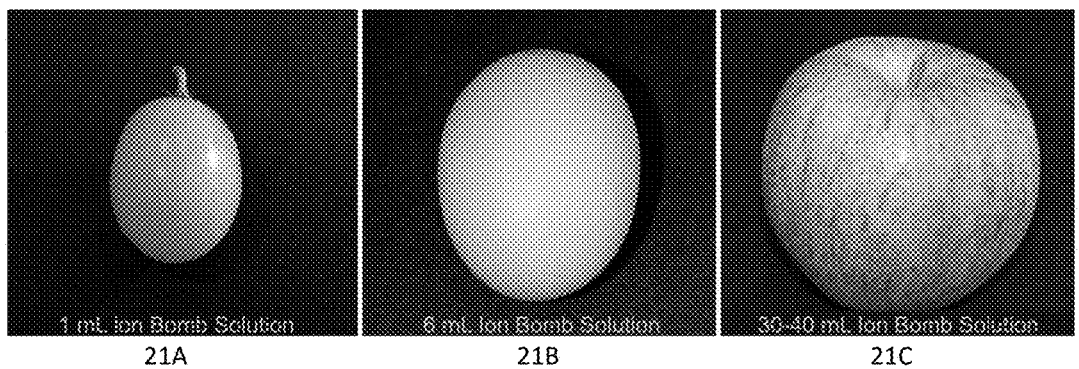
FIG. 21A. The picture of a large grape at 25mm ×25mm ×30mm in size (weighing 10.1 grams (g). Clinically, such size of a cancer or tumor is killed by one single intratumoral injection with 1.0ml of the "medicinal ion bomb.
" FIG. 21B. The picture of an egg at 45mm ×45mm ×60mm in size (weighing 69g), requiring approximately 6.0ml of the "medicinal ion bomb" for an intratumoral treatment.
FIG. 21C. The picture of a fresh Gala apple at 70mm ×70mm ×80mm in size (weighing 290g), which needs about 30ml to 40ml of the "medicinal ion bomb" for an intratumoral injection.

FIG. 21. This group of pictures is the description of clinical data of the invention that is useful for clinical investigator, physician and oncologist to plan the required amount of the "medicinal ion bomb" solution in different sizes of tumor. FIG. 21A was a picture of a large grape at 25mm×2.5mm×30mm in size (weighing 10.1g). Clinically, such size of a cancer or benign tumor is killed by one single intratumoral injection with 1.0ml of the "medicinal ion bomb" solution. FIG. 21B was a picture of an egg at 45mm×45mm×60mm in size (weighing 69g), requiring approximately 6.0ml of the "medicinal ion bomb" solution for the treatment. FIG. 21C was a picture of a fresh Gala apple at 70mm×70mm×80mm in size (weighing 290g), which needs about 30ml to 40ml of the "medicinal ion bomb" solution.

Tissue Damage in the Injection Site of the "Medicinal Ion Bomb" Solution

Intramuscular injection with the "medicinal ion bomb" solution only caused mild injury to normal muscular tissue at the injection site. Microscopically, there was unremarkable damage to muscular tissue except transient infiltration of inflammatory cells.

Acute Toxicity Test and Chronic Toxicity Test of the "Medicinal Ion Bomb"

Acute toxicity test, including liver function, kidney function, pancreatic and pulmonary functions, and blood electrolytes ($Na^+$, $K^+$ and $Ca^{2+}$), were examined in rats.

Thirty-six normal SD rats weighing 220±g were divided into 5 groups with 4 animals in the control group and 8 rats in each experimental group. Each animal in the control group received 1.0ml of normal saline through intramuscular injection (the same amount of the "medicinal ion bomb" solution as in the experimental groups). Animals in experimental groups 2, 3, 4 and 5 were treated through intramuscular injection with 1.0ml of the "medicinal ion bomb" solution (the MTD "medicinal ion bomb" solution containing 20μg/ml adrenaline) in rats.

Animals in Group 1 served as the controls and they were killed for artery (abdominal aorta) blood sample on day zero. For acute toxicity test, animals in Group 2 were sampled on day one; animals in Group 3 were sampled on day two; and animals in Group 4 were sampled on day three after treatment. For chronic toxicity test, animals in Group 5 were sampled on day 66 after treatment. The laboratory parameters include:

Liver function (blood ALT, total bilirubin, and total protein)
Kidney function (blood urea nitrogen, BUN)
Pancreatic function (blood sugar reflects partially pancreatic function)
Lung function (partial pressure $CO_2$, $PCO_2$) and
Electrolytes ($K^+$, $Na^+$ and $Ca^{2+}$).

Samples were tested using a Hitachi Automatic Biochemical Analyzer 717 (Roche Diagnostics).

Data from the control group and experimental groups were expressed as mean values±SD. Results between the normal control group and experimental groups were compared by analysis of variance and Student's t-test using EXCEL statistical software. A p value <0.05 was considered statistically significant, with p<0.01 being highly significant.

Liver

Figure 22:
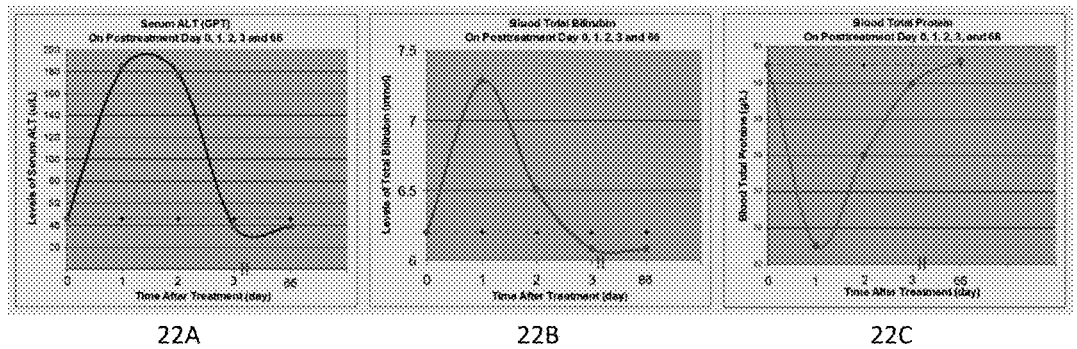
FIG. 22A. The data of acute toxicity test of the "medicinal ion bomb" to the liver in Sprague Daley (SD) rats. The mildly elevated blood ALT returned to normal range by 4 days after intramuscular injection with the MTD of the "medicinal ion bomb.
" FIG. 22B. Normal blood total bilirubin after treatment.
FIG. 22C. Normal plasma total protein.

The results showed that when the MTD "medicinal ion bomb" solution was intramuscularly administered, the "medicinal ion bomb" solution caused transiently mild injury to the liver function that was recovered in 4 days after treatment. For the detailed data, see FIG. 22. FIG. 22A. For acute toxicity test of liver function, elevated level of blood ALT is seen in one and two days after treatment, and it returned to normal range in 4 days after treatment. FIG. 22B. Normal blood total bilirubin. FIG. 22C. Normal blood total protein. These parameters indicated that increased level of blood ALT was transient, indicating that the "medicinal ion bomb" has not caused acute toxicity to liver function.

Sixty-six days after treatment, levels of blood ALT, bilirubin, and total protein were in normal ranges, there was no evidence of chronic liver toxicity caused by the "medicinal ion bomb."

Kidney

Figure 23:
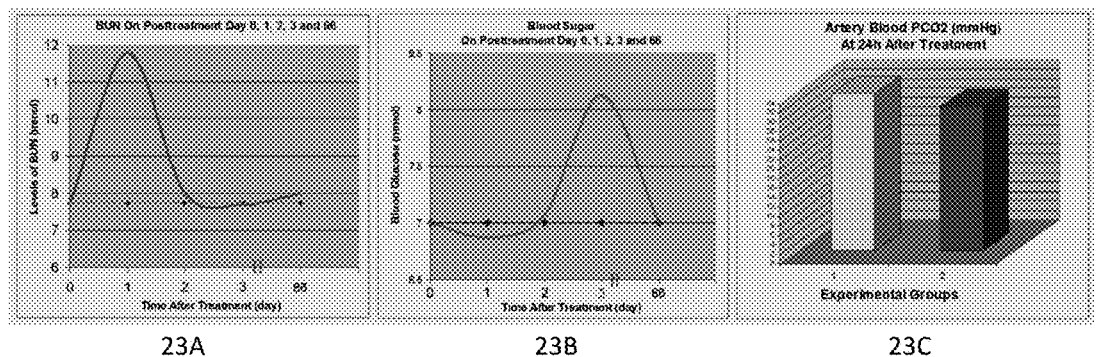
FIG. 23. No biochemical evidence of the "medicinal ion bomb" caused acute toxicity to lung, pancreas and kidney.

FIG. 23A. Normal blood BUN.

Pancreas

The level of blood sugar partially reflects the function of the pancreas. One and 2 days after treatment, the level of blood sugar was in normal range. As shown in FIG. 23B. No evidence of chronic toxicity of the "medicinal ion bomb" to the pancreas.

Lung $PCO_2$ was only tested on day one after treatment. As seen in FIG. 23C, there was no significant difference in $PCO_2$ between the control level and posttreatment one, indicating that there was no acute toxicity of the MTD "medicinal ion bomb" treatment to lung function. FIG. 23C. The yellow column was $PCO_2$ in the control group and blue column was $PCO_2$ in the experimental group treated with the MTD "medicinal ion bomb" solution. Making comparison of $PCO_2$ levels between the control group and experimental groups, P>0.05 and there was no statistical difference.

The affect of the "medicinal ion bomb" on heart rate, blood pressure and breathing was examined in SD rats during and after treatment using a computer-assisted Buxco Max II Biosystem (Buxco Electronics, Sharon, Conn.). No abnormal findings were found in the above 3 parameters.

It must point out that the results of these parameters are resulted from the MTD "medicinal ion bomb." This is not an issue in clinical practice. Generally, the dimension of a treated human tumor is smaller than 10cm×10cm in diameters that the amount of the "medicinal ion bomb" is much less than the MTD. Therefore, the transiently elevated level of ALT from the MTD "medicinal ion bomb" can be ignored.

Pharmacokinetics of the "Ion Bomb Solution"

Figure 24:
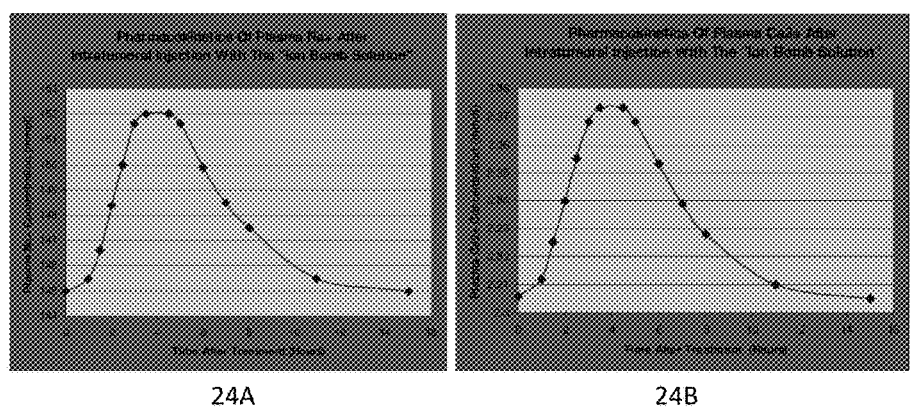
FIGS. 24A and 24B. Pharmacokinetic patterns of plasma $Na^+$ and $Ca^{2+}$, and time points of ascending concentrations of plasma $Na^+$ and $Ca^{2+}$ to 50%, 63% and 95%, and time points of elimination concentrations of plasma $Na^+$ and $Ca^{2+}$ to 50%, 37% and 5% in the model of intramuscular injection with the "medicinal ion bomb" in SD rats.

Pharmacokinetic models predict the time dependence of a drug's concentration in the body fluids following its administration. Pharmacokinetics is mainly divided into four areas including the extent and rate of absorption, distribution, metabolism and excretion (ADME). FIG. 24 showed preliminary result of pharmacokinetics of intratumoral injection with the "medicinal ion bomb solution" in rats.

Sixty SD rats, both genders, weighing 200±g, were randomly divided into 30 subgroups with 2 animals in each subgroup. Animals in the control group received 0.5ml of normal saline intramuscularly. All animals in experimental groups received intramuscular injection with 0.5ml of the "medicinal ion bomb" solution (containing 20μg/ml adrenaline) in the buttock (the MTD of the "medicinal ion bomb" solution in rat weighing 200±g is 1.0ml. In this experiment, the ½ amount of the MTD "medicinal ion bomb solution" was used). Blood samples were obtained through the abdominal aorta at an interval of every 30 minutes, consecutively from the start time point 0 to the end time point of 15 hours after treatment. The concentrations of plasma $Na^+$ and $Ca^{2+}$ in blood samples were analyzed using a Hitachi Automatic Biochemical Analyzer 717. Statistically, mean values of the control group and all experimental groups were used to plot the pharmacokinetic patterns of plasma $Na^+$ and $Ca^{2+}$.

As shown in FIG. 24, the ascending concentrations of plasma $Na^+$ to 50%, 63% and 95% were found at posttreatment points of 2.0, 2.5 and 3.0 hours, respectively. The peak level of plasma $Na^+$ was detected at 3.5 hours after treatment. The levels of plasma $Na^+$ were decayed to 50%, 37% and 5% at 7.0, 8.0 and 11 hours after treatment, respectively.

The ascending concentrations of plasma $Ca^{2+}$ to 50%, 63% and 95% were at posttreatment points of 2.0, 2.5 and 3.0 hours, respectively. It decayed to 50%, 37% and 5% at posttreatment points of 7.0, 8.0 and 11 hours, respectively.

The data showed that 95% clearance of the injected $Na^+$ and $Ca^{2+}$ from blood was seen at 11 hours after intramuscular injection with the "medicinal ion bomb." Most of NaCl and $CaCl_2$ are excreted through the kidney and gastrointestinal tract. Both concentrations of plasma $Na^+$ and $Ca^{2+}$ returned to the control levels at 15 hours after intramuscular injection.

FIGS. 24A and 24B show the time points of the ascending concentrations of plasma $Na^+$ and $Ca^{2+}$ to 50%, 63% and 95% and the time points of the elimination concentrations of plasma $Na^+$ and $Ca^{2+}$ to 50%, 37% and 5% in the model of intratumoral injection with the "medicinal ion bomb" solution in SD rat.

Half-Life of Plasma $Na^+$ and $Ca^{2+}$ from the "Medicinal Ion Bomb" Solution

A biological half-life or elimination half-life is the time that it takes for a drug to lose one-half of its pharmacologic activity. As shown in FIG. 24, the half-life of plasma $Na^+$ and $Ca^{2+}$ from the "medicinal ion bomb" solution was detected at 7.0 hours after intratumoral injection in SD rat.

Pharmacodynamic Study on the "Medicinal Ion Bomb Solution"

Pharmacodynamic models deal with the action of the drug once it reaches its target organ. Pharmacodynamic actions of the "medicinal ion bomb" solution to kill cancer cells are multiple-directions. However, as shown by the data of the patch clamp technique, fluorescent $Na^+$ and $Ca^{2+}$ channel probe monitoring, the real-time microscopic video, pathology and SEM and TEM, the "medicinal ion bomb" mainly targets the membrane, nucleus as well as tumor vessels.

The cell membrane is a biological membrane that separates the interior of all cells from the outside environment. The cell membrane is selectively permeable to ions and organic molecules, and controls the movement of substances in and out of cells. The basic function of the cell membrane is to protect the cell from its surroundings. If the membrane of a cell is damaged or broken, the cell is dead.

Membrane potential is the difference in electric potential between the interior and exterior of a cell. Membrane potential of cells can be measured by the patch clamp technique that allows the study of single or multiple ion channels in cells, especially it is used in the study of excitable cells such as neurons, cardiomyocytes, muscle fibers and pancreatic beta cells. Changes in membrane potential can also be used to evaluate the death of cardiomyocyte in vitro.

Previously, we introduced the application of the patch clamp technique in determination of membrane potential of mouse cardiomyocyte. When a low concentration of the "medicinal ion bomb" solution was administered, death of treated cells is characterized by a sub-acute pathologic process. For example, the mouse cardiomyocyte was killed in 5 minutes after treatment with 5% concentration (252.4 mM of $Na^+$ and 12.5 mM of $Ca^{2+}$) of the "medicinal ion bomb" solution. The mouse cardiomyocyte was dead in 3 minutes after treatment with 10% concentration (504.79 mM of $Na^+$ and 25 mM of $Ca^{2+}$) of the "medicinal ion bomb solution". When the 100% "medicinal ion bomb" solution (5.0479 M of $Na^+$ and 250 mM of $Ca^{2+}$) was used, death of treated cancer cells is characterized by an acute pathologic process. Under the real-time inverted microscope, MCF7 human breast cancer cells in tissue culture were killed in 12 to 18 seconds in 100% "medicinal ion bomb" solution. This fact indicates that pharmacodynamic action of the "medicinal ion bomb" solution to kill cancer cells was a dose-and-time dependent.

Histopathologic Study on Vital Organs

Histopathologic study was performed on 6 vital organs in mice treated with the "medicinal ion bomb." Specimens were taken 24 hours after treatment with the "medicinal ion bomb" solution and fixed in formalin, embedded in paraffin, stained with hematoxylin and eosin, and read under a digital light microscope by two experienced pathologists. The data disclosed that the treated animals didn't show evidence of pathologic damage to heart, lung, liver, kidney, pancreas and uterus.

Figure 25:
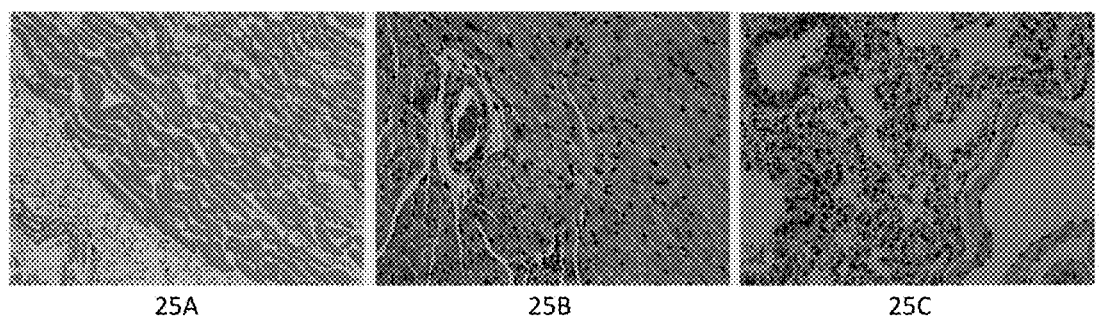
FIG. 25. No evidence of pathologic damage of the "medicinal ion bom " to heart, lung, liver, kidney, pancreas and muscular tissue at the injection site in mice. Magnification ×200.
Figure 25:
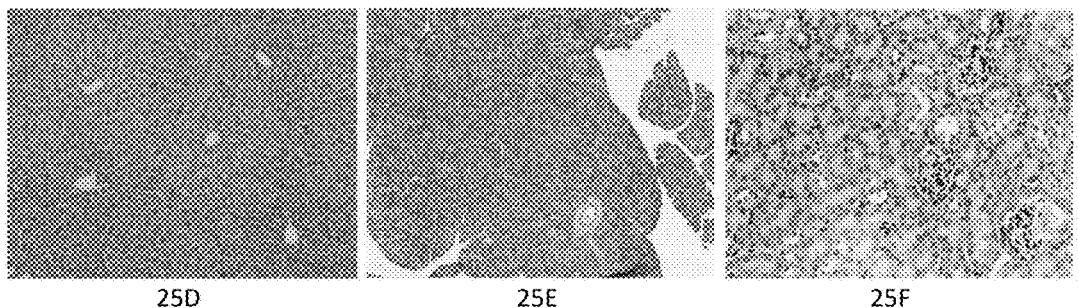

FIG. 25A was a muscular tissue from the injection site of the "medicinal ion bomb" solution in mouse. The muscular tissue showed mild injury with infiltration of inflammatory cells. FIG. 25B. Normal microscopic feature of the heart. FIG. 25C. Normal lung. Magnifications ×200.

FIGS. 25D-25F showed normal microscopic features of the liver, pancreas and kidney. Magnifications ×200.

Figure 26:
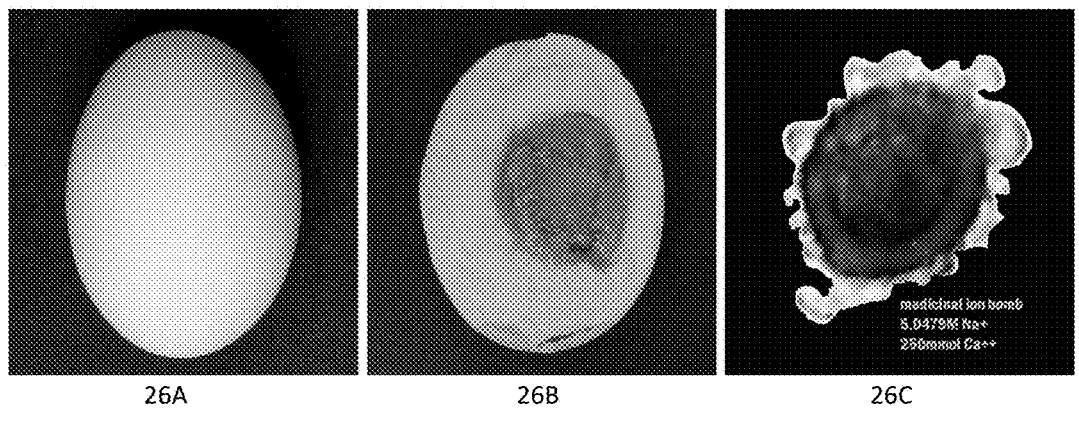
FIG. 26 explains historic background of the invention of the "medicinal ion bom."
Figure 27:
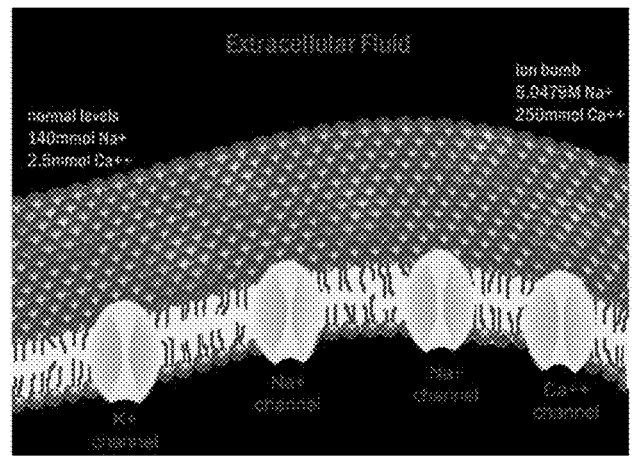
FIG. 27. A diagram of a segment of cell membrane to teach the theory and mechanism of development of the "medicinal ion bom " by comparison of levels of $Na^+$, $Ca^{2+}$ and $K^+$ between the extracellular fluid and the "medicinal ion bomb."

Theory and Mechanism of the "Medicinal Ion Bomb" for Treating Cancer, Tumor and Neoplasm Regarding the theory and mechanism of the "medicinal ion bomb" for cancer treatment, as shown in FIGS. 26 and 27, they are related to biochemistry, cell biology, cell physiology, cell membrane, cellular membrane potential, ion channels, ion tracking techniques, and the formula of the "medicinal ion bomb" solution using high concentrations of $Na^+$ and $Ca^{2+}$ between the extracellular and intracellular fluids.

In cell physiology, survival of normal cells, tumor cells or cancer cells is dependent upon the equilibrium of osmotic pressure inside and outside of cells. Normal osmotic pressure of cells depends on the equilibrium of concentrations of ions between the extracellular and intracellular fluids. When concentrations of ions between the extracellular and intracellular fluids are identical, it is called isotonic. Since the cell is at equilibrium, there is no ionic concentration gradient, and the flow of water in is equal to the flow of water out. This does not cause sickness or death of the cell.

In physiological condition, the concentration of $Na^+$ in the extracellular fluid is 140 mM and intracellular fluid is 14 mM. Because the "medicinal ion bomb" solution has 5.0479 M of $Na^+$ the concentration of $Na^+$ in the extracellular fluid of cancer cells is 36-fold higher than the normal level, and the concentration of $Na^+$ in the intracellular fluid is about 360-fold higher than the normal concentration. When a large amount of $Na^+$ crosses the cell membranes from the extracellular fluid to intracellular fluid, cancer cells are killed in dozen seconds by overwhelming influx of high concentration of $Na^+$ from the "medicinal ion bomb" (FIGS. 26 and 27). This theory has been proven by the patch clamp technique for membrane potential and fluorescent labeled ion probe monitor system.

FIG. 26A was a salted duck egg which was prepared with sodium chloride 2 years ago. FIG. 26B showed a salted duck egg which has been cooked and cut. Its albumin and yolk were not rotted even though it was preserved at room temperature for 2 years. FIG. 26C showed a picture of a cancer cell and the "medicinal ion bomb" comprising 5.0479 M of $Na^+$ and 250 mM of $Ca^{2+}$ in the extracellular fluid.

Figure 29:
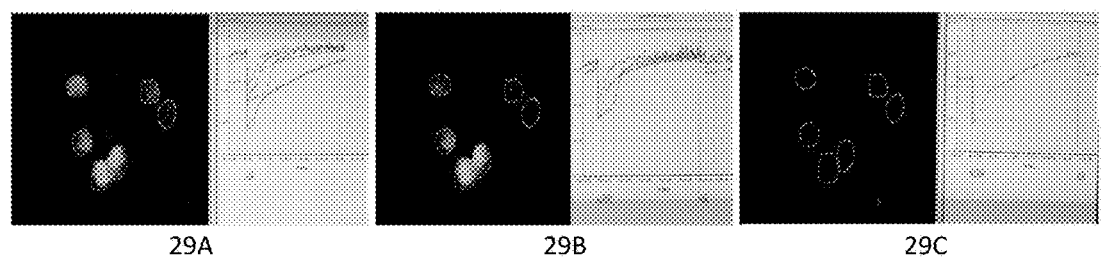
FIG. 29. A group of dynamic drawings of $Na^+$ influx using the fluorescent labeled $Na^+$ probe technique in MCF7 human breast cancer cells.
Figure 30:
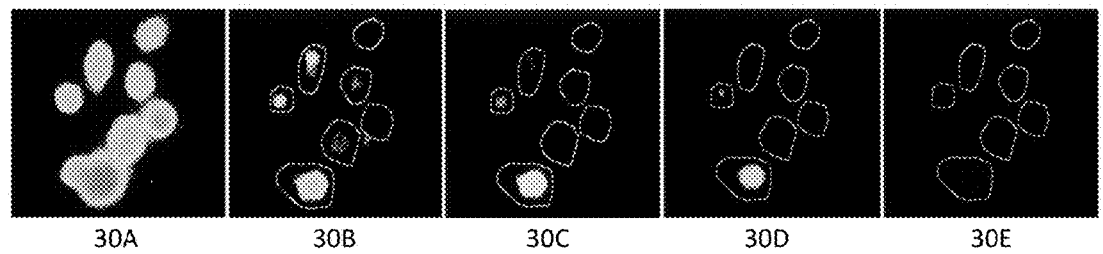
FIG. 30. A group of dynamic drawings of $Ca^{2+}$ influx using the fluorescent labeled $Ca^{2+}$ probe technique in MCF7 human breast cancer cells.

On the other hand, the normal concentration of $Ca^{2+}$ in the extracellular fluid is 2.5 mM and intracellular fluid is 0.0001 mM in mammalian cells. The "medicinal ion bomb" contains 250 mM of $Ca^{2+}$ which is 100-fold higher than its physiological level in the extracellular fluid and approximately 2.5 million-fold higher than its physiological concentration in the intracellular fluid. As a result, when a high concentration of $Ca^{2+}$ overwhelmingly crosses cell membrane from the extracellular fluid to intracellular fluid, cancer cells are killed immediately. This theory has also been confirmed by the patch clamp technique and ionic tracking techniques in the invention (FIGS. 28-30).

FIG. 27 showed a fragment of the cell membrane where normal levels of $Na^+$ and $Ca^{2+}$ in the extracellular fluid and high concentrations of $Na^+$ and $Ca^{2+}$ in the "medicinal ion bomb" are seen. Channels of $Na^+$, $Ca^{2+}$, $K^+$ and others are embedded in the cell membrane. When extremely high levels of $Na^+$ and $Ca^{2+}$ influx from the extracellular fluid to intracellular fluid, cancer cells are killed in dozen seconds.

More importantly, $Ca^{2+}$ is one of secondary messengers in cell signal transduction biology. High concentration of $Ca^{2+}$ in the intracellular fluid not only causes tremendous physiological damages, but also causes huge biological actions to cancer cells. Therefore, high concentration of $Ca^{2+}$ in the "medicinal ion bomb" solution can accelerate death of cancer cells and it is regarded as the enhancer of cancer-killing.

Figure 28:
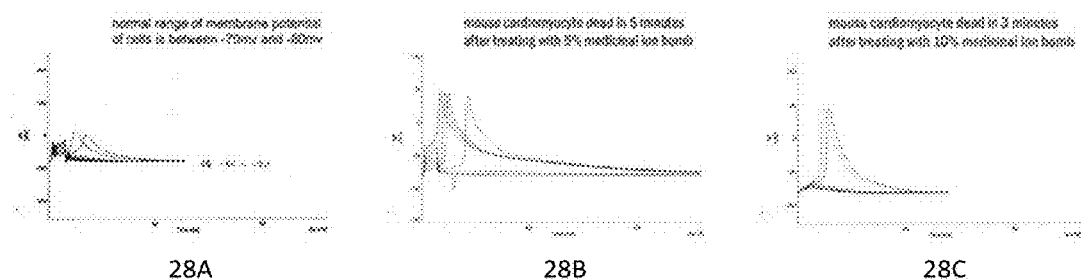
FIG. 28. Three drawings of the patch clamp technique in testing the membrane potential of mouse cardiomyocyte treated with different concentrations of the "medicinal ion bomb.

FIG. 28. Three drawings of the patch clamp technique in testing of the membrane potential of mouse cardiomyocytes treated with different concentrations of the "medicinal ion bomb" solution. FIG. 28A. The control membrane potential of a normal mouse cardiomyocyte in TyRode solution. FIG. 28B. A mouse cardiomyocyte died by in 5 minutes after treatment with 5% concentration of the "medicinal ion bomb" solution. FIG. 28C. A mouse cardiomyocyte died by 3 minutes after treatment with 10% concentration of the "medicinal ion bomb" solution. The data demonstrated that the killing action of the "medicinal ion bomb" solution to cancer cells was a dose-and-time dependent.

FIG. 29. A group of dynamic pictures of $Na^+$ influx using fluorescent labeled $Na^+$ channel probe system. FIG. 29A showed the gated 6 pretreatment MCF7 human breast cancer cells. FIG. 29B demonstrates that 2 of them died by 10 seconds after starting treatment with the "medicinal ion bomb" solution. FIG. 29C. All gated cancer cells are died by 16 seconds after starting the treatment with the "medicinal ion bomb" solution. These images were counterparts from the monitor of a Macintosh computer.

FIG. 30 was a group of dynamic pictures of $Ca^{2+}$ influx using fluorescent labeled $Ca^{2+}$ channel probe system in MCF7 human breast cancer cells. FIG. 30A. The gated 7 cancer cells before treatment. FIG. 30B. Two of 7 cancer cells are died by 9 seconds after starting the treatment with the "medicinal ion bomb." FIG. 30C. Four of 7 cancer cells died by 12 seconds after starting treatment. FIG. 30D. Five of 7 cancer cells died by 16 seconds after starting treatment.

FIG. 30E. All 7 cancer cells were killed by 18±seconds after starting treatment. These data suggested that there was an individual difference in sensitiveness of cancer cells to the "medicinal ion bomb" These images were counterparts from the monitor of a Macintosh computer.

Enhance Cancer-Killing Actions of the Combination of $Na^+$ and $Ca^{2+}$

In this invention, we studied the influx of $Na^+$ and $Ca^{2+}$ from the extracellular fluid into intracellular fluid of cancer cells was studied. The fluorescent $Na^+$ or $Ca^{2+}$ probe monitoring showed that use of 5.0479 M of $Na^+$ solution alone took 20±4 seconds to kill MCF7 human breast cancer cells. When the "medicinal ion bomb" solution was used, it only took 18±4 seconds to kill the same type of cancer cells, which indicates that $Ca^{2+}$ has an enhancer effect in cancer treatment.

The diffusion of $Na^+$ in tumor tissue in living animals was fast and diffusion of $Ca^{2+}$ was slow, and both types of ions in high concentration were capable of killing cancers when they were used separately. Further, we have found that the combination of $Na^+$ and $Ca^{2+}$ in the formulation of the "medicinal ion bomb" has synergetic, complementary and dual-wave cancer-killing effects. The first wave of cancer-killing effects (the early killing action) was mediated by $Na^+$, which happens in one to 12 hours after treatment. The second wave of cancer-killing action (the later killing effect) was mediated by $Ca^{2+}$, that occured in 6 to 24 hours after treatment.

Five Phases of the "Medicinal Ion Bomb" to Kill Cancer Cells

Figure 31:
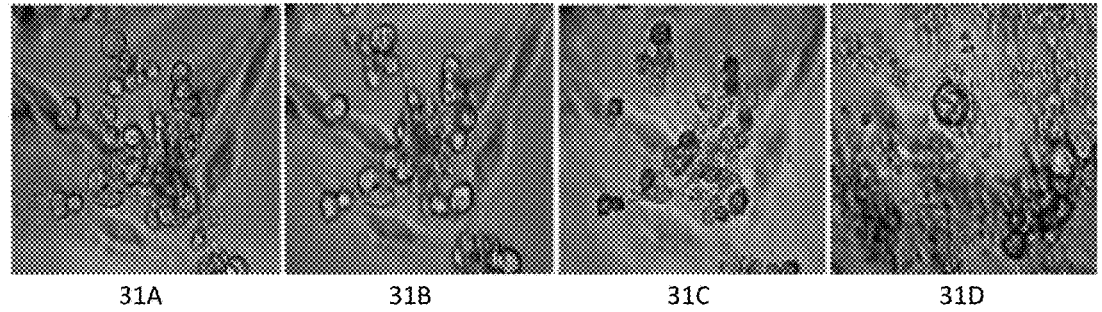
FIG. 31. Four micrographs of dynamic real-time inverted microscopy in a group of MCF7 human breast cancer cells in tissue culture chamber.
Figure 32:
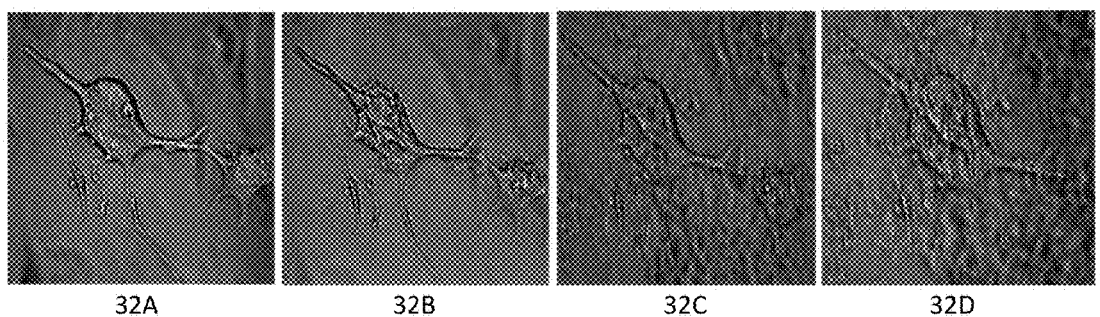
FIG. 32. Four micrographs of dynamic real-time inverted microscopy in a single MCF7 human breast cancer cell treated with the "medicinal ion bomb" in tissue culture chamber, representing 4 consecutively pathologic courses.
Figure 33:
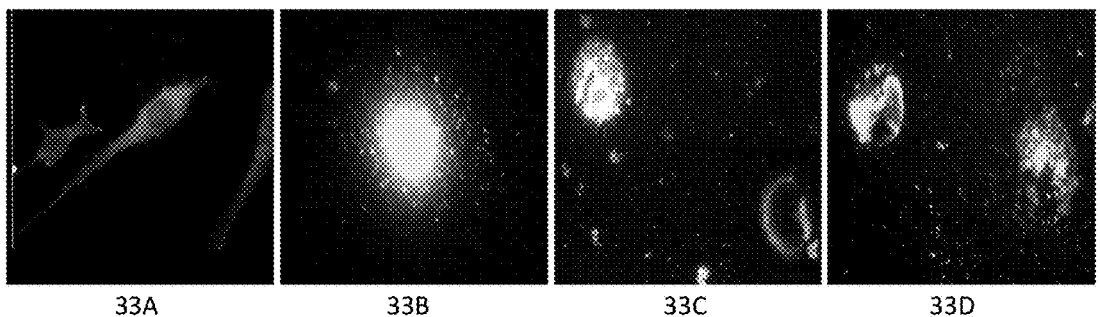
FIG. 33. A group of micrographs of real-time inverted microscopy.

Video data of real-time inverted microscopy revealed 5 pathologic phases of the "medicinal ion bomb" to kill cancer cells: (1) Rapid damage to membrane of cancer cells; (2) acute intracellular dehydration of cancer cells because of high concentrations of $Na^+$ and $Ca^{2+}$ in the extracellular fluid from adding the "medicinal ion bomb" into the cell culture chamber; (3) swelling of cancer cells due to overwhelming influx of large amounts of $Na^+$ and $Ca^{2+}$ in the extracellular fluid from the "medicinal ion bomb" into intracellular fluid; (4) bursting of cancer cells caused by extreme edema; and (5) death of cancer cells. The entire process of 5 pathologic phase to cancer cells occurred in dozen seconds and each of pathologic phases occurred only in 3 to 4 seconds (FIGS. 31-33).

Pathology Findings

Macroscopically, the human cancer treated underwent 4 pathologic features. (1) From 1 to 12 hours after treatment, cancer tissue experiences in situ degeneration and necrosis and collapse of tumor vessels. Surface of the treated tumor appears light blue. (2) If a tumor or cancer was smaller than 10mm×10mm in size, it would be completely removed by one intratumoral injection with the "medicinal ion bomb" in 24 to 48 hours. When a tumor or cancer was larger than 20mm×20mm in size, the treated tumor developed coagulative necrosis that caused a charred and dead tumor remainder. (3) The dead tumor or cancer remainder came off and left a small wound by 7 to 10 days after treatment. (4) The wound of the treated tumor was healed by 2 to 3 weeks posttreatment.

Microscopic findings of human cancer treated with the "medicinal ion bomb" were featured: (I) $Na^+$ and $Ca^{2+}$ salts contributed in the surrounding tissue of cancer cells (II) necrosis of tumor tissue or cancer tissue was seen where the "medicinal ion bomb" reached, indicating that fully filling a tumor with the "medicinal ion bomb" solution is a necessary factor to reach completely kill a solid cancer; (III) multiple thrombi in tumor vessels; and (IV) massive bleeding in necrotic areas resulted from injured tumor vasculatures.

FIG. 31. A group of dynamic micrographs of real-time inverted microscopy on a cluster of MCF7 human breast cancer cells treated by the "medicinal ion bomb" in tissue culture chamber. FIG. 31A. The pretreatment cancer cells as the control. FIG. 31B. Slight changes in cell morphology were seen 3 seconds after starting treatment with the "medicinal ion bomb." FIG. 31C. All cancer cells were heavily damaged 5 seconds after starting treatment. FIG. 31D. All cancer cells died by 16 seconds after starting treatment. Magnification ×200.

FIG. 32 was a group of dynamic micrographs of real-time inverted microscopy on one MCF7 human breast cancer cell treated with the "medicinal ion bomb" in cell culture chamber. FIG. 32A. A pretreatment cancer cell served as the control. FIG. 32B. Acute intracellular dehydration of the treated cancer cell by 6 seconds after starting treatment. FIG. 32C. Highly edema of the cell and damaged membrane of the cancer cell were seen by 12 seconds after starting the treatment. FIG. 32D. Membrane of the cell was broken and a dead cancer cell was seen by 16 seconds after starting the treatment. Magnifications ×400.

FIG. 33 was a group of micrographs of real-time inverted microscopy. FIG. 33A was a micrograph of untreated cancer cells as the control. FIG. 33B. Burst of a highly swollen cancer cell treated with the "medicinal ion bomb." FIG. 33C. Two completely damaged cancer cells treated by the "medicinal ion bomb." One cell on the upper part of the field showed a large rupture in the membrane of the cell. The entire cell looked like a rotten pineapple. A cell in the lower part of the micrograph lost its cytoplasm, nucleus, and intracellular components. FIG. 33D. Two completely destroyed cancer cells. Both upper and lower parts of the cell were defected. Microscopically, these pathologic features looked like the sites where a nuclear bombing occurred. Magnifications ×400.

Figure 34:
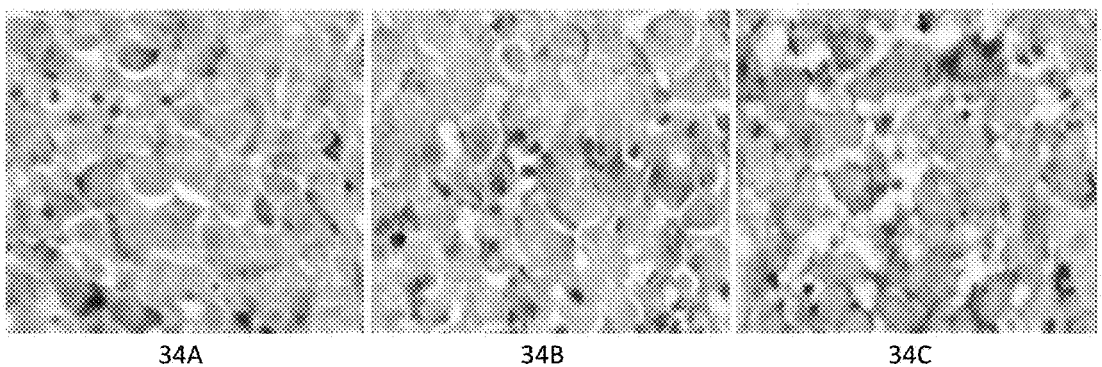
FIG. 34. In vivo distribution of the "medicinal ion bom" (white lines) surrounding cancer cells in a treated mouse cancer model.

FIG. 34A and 34B demonstrated 2 tumor sections that were fully filled with the "medicinal ion bomb." FIG. 34C Crystal structures of $Na^+$ and $Ca^{2+}$ salts contributed in intercellular gaps that looked like white lines surrounding cancer cells. Magnifications ×1000.

Figure 35:
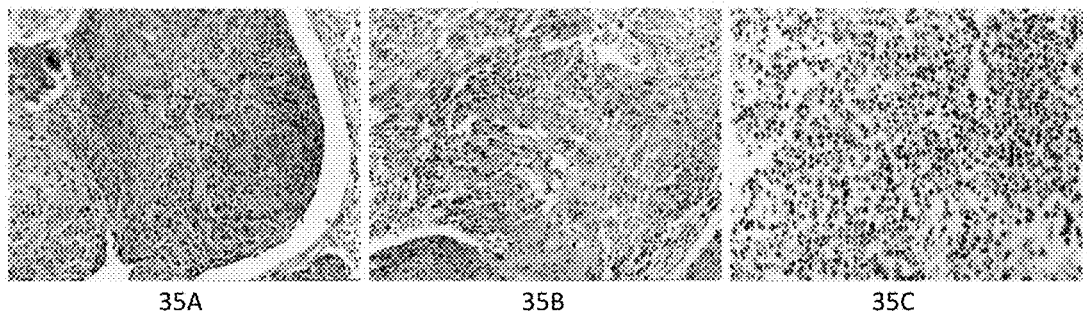
FIG. 35. A group of micrographs of light microscopy of a mouse adenocarcinoma treated by the "medicinal ion bomb.

FIG. 35 was a group of micrographs of light microscopy on a MC38 mouse adenocarcinoma treated by intratumoral injection with the "medicinal ion bomb." The specimen was taken one day after the treatment. FIG. 35A. A pretreatment tumor as the control. FIG. 35B. A specimen taken from the margin of a treated tumor where there still was a small area of living cancer tissue, indicating that the treated tumor tissue was not fully filled with the "medicinal ion bomb." FIG. 35C. A mouse tumor model where all tumor tissue was completely killed indicating that fully filling a cancer lesion with the "medicinal ion bomb" was a necessary factor to reach a completely kill a cancer. Magnifications ×200.

Figure 36:
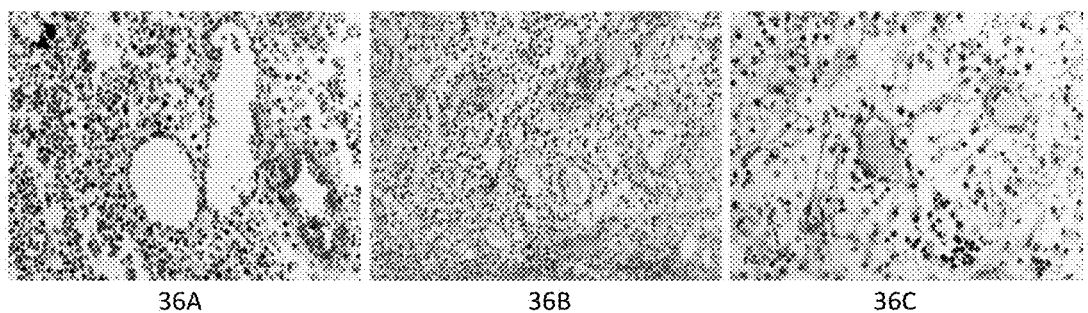
FIG. 36. Pathologic findings of light microscopy in a patient suffered from maxillary sinus carcinoma.

FIG. 36 Pathological findings of light microscopy in a patient suffered from maxillary sinus carcinoma. The specimen was taken 3 days after the treatment with the "medicinal ion bomb." FIG. 36A. All tumor tissue was completely killed and associated with inflammatory reactions and congestion of the treated cancer tissue. Red blood cells were lining on the inner lumen of blood vessels. Magnification ×400. FIG. 36B. Multiple thrombi in tumor vessels. Magnification ×200. FIG. 36C. A typical thrombus in a small vein. Magnification ×400.

Electron Microscopic Findings

Figure 37:
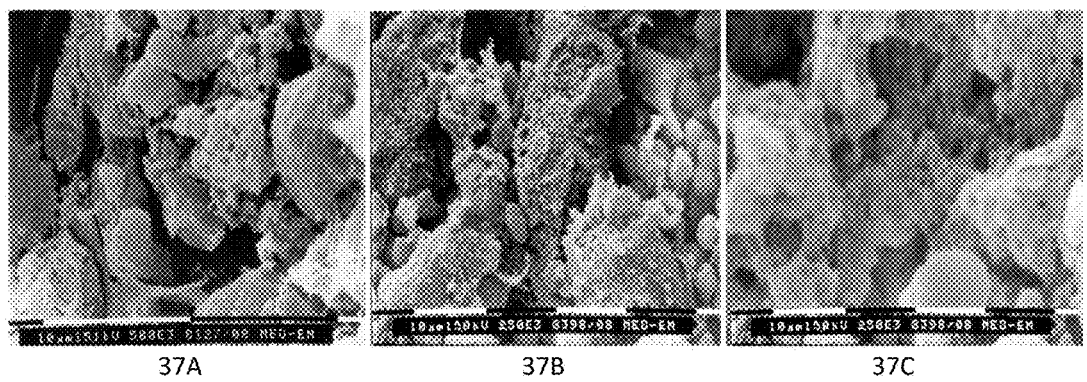
FIG. 37. A group of micrographs of SEM of cell membranes in a MCF7 human breast cancer model in nude mice.

FIG. 37 was a group of micrographs of SEM of cell membranes in a MCF7 human breast cancer model in nude mouse. FIG. 37A. A control tumor in which membranes of cancer cells were smooth. FIG. 37B. Membranes of cancer cells treated with the "medicinal ion bomb" were cavernous. FIG. 37C. Volcanic crater features of treated cancer tissue. Magnification ×2000.

Figure 38:
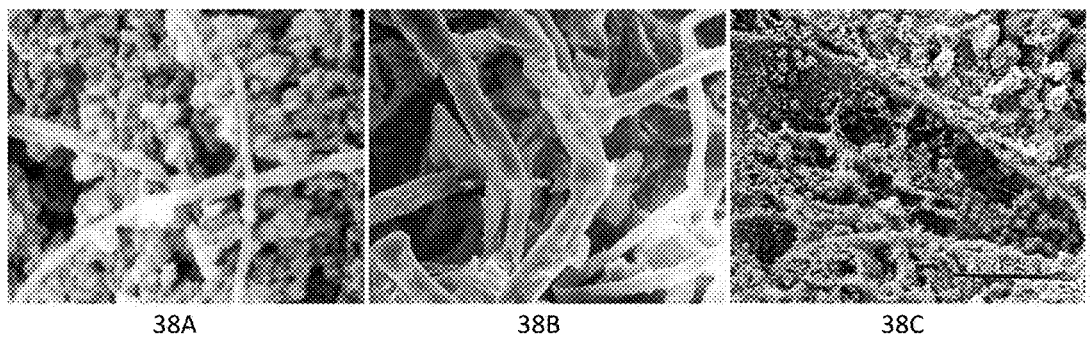
FIG. 38. A group of micrographs of SEM of tumor vessels in a MCF7 human breast cancer model in nude mice.

FIG. 38 was a group of micrographs of SEM of tumor vessels in a MCF7 human breast cancer model in nude mice. FIG. 38A. Control tumor vessels looked like lotus-roots and surface of tumor vessels were smooth. Magnification ×1000. FIG. 38B. The outer layer, median layer and inner layer structures of arterioles and venules had multiple ruptures. Magnification ×2000. FIG. 38C. A lot of protein materials and blood cell components in a damaged large vascular lumen. Magnification ×1000.

Figure 39:
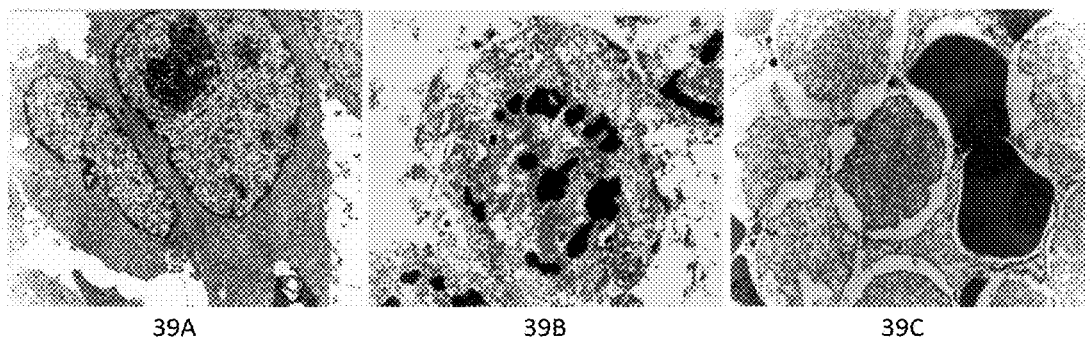
FIG. 39. Micrographs of TEM of control cancer cells and treated cancer cells in MCF7 human breast cancer model in nude mice.

FIG. 39. Micrographs of TEM in the control cancer and treated human breast cancer models in nude mice. FIG. 39A. Two untreated cancer cells as the control. FIG. 39B. A damaged cancer cell. Membrane, nucleus and chromatins of the cell were heavily damaged. Ultrastructures of cytoplasm organelles, cytoskeleton, mitochondria, and lysosome were collapsed. FIG. 39C. This was a representative micrograph of TEM to demonstrate in vivo distribution of the ¢medicinal ion bomb" in a treated human breast cancer model in nude mouse. In this field there were 9 cancer cells. Four of them showed their entire cell morphology that looked like four pieces of Christmas hats. White brims surrounding 4 pieces of "Christmas hats" were the in vivo distribution of $Na^+$ and $Ca2^+$ salts in cancer tissue treated. Magnification ×2000.

Figure 40:
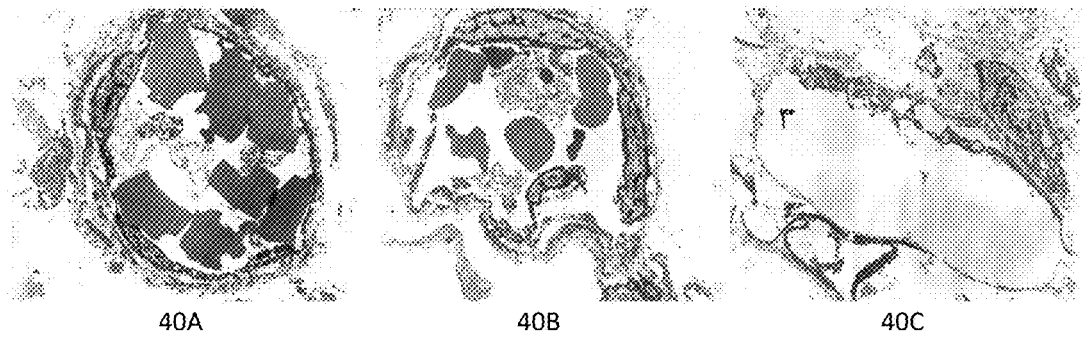
FIG. 40. A group of micrographs of TEM of damaged tumor vessels in MCF7 human breast cancer models in nude mice.

FIG. 40 is a group of migraphs of TEM of damaged tumor vessels. FIG. 40A. An injured arteriole. The outer layer, median layer and inner layer of the arteriole had multiple breaks. On the left upper part of the micrograph, an injured endothelial cell was split off from the inner lumen. Seven irregular dark objects in the arteriole lumen were deformed red blood cells. Two red blood cells were crossing the defected vascular wall to outside of the vascular lumen. Magnification ×2000. FIG. 40B. On the lower part of the micrograph and injured endothelium was coming off from the inner wall of an injured arteriole. FIG. 40C. An injured venule with multiple breaks. Magnification ×2000.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A pharmaceutical composition comprising 5.0479 M to 5.5 M of $Na^+$, 250 mM to 2.0 M of $Ca^{2+}$, an appropriate amount of distilled water, 10 ml of iopromide, 20 mg of adrenaline at room temperature, for use in an intratumoral injection treatment of malignant tumor and cancer, benign tumor and non-malignant disease.

2. The pharmaceutical composition of claim 1, wherein the effective treatment amount of $N^+$ is 5.0479 M and the effective treatment amount of $Ca^{2+}$ is 250 mM in an aqueous solution at room temperature.

3. The pharmaceutical composition of claim 1, wherein the $Na^+$ source for the intratumoral injection treatment is NaCl and organic sodium salt.

4. The pharmaceutical composition of claim 1, wherein the $Ca^{2+}$ source for the intratumoral injection treatment is CaCl and organic calcium salt.

5. The pharmaceutical formulation of claim 1 used in treating a patient with malignant tumor and cancer condition selected from the group consisting of cancer of brain, thyroid, breast, lung, liver, pancreas, kidney, colon and rectum, ovary and prostate, uterus and cervix, skin and subcutaneous tissue.

6. The pharmaceutical formulation of claim 1 used in treating a patient with benign tumor and non-malignancy selected from the group consisting of adenoma, angioma, atheroma, fibroma, lipoma, thymoma, cyst, polyp, skin neoplasm, breast fibrocystic change, benign prostatic hyperplasia, thyroid nodule and hyperthyroidism.

* * * * *